US009248001B2

(12) United States Patent
Colombet et al.

(10) Patent No.: US 9,248,001 B2
(45) Date of Patent: Feb. 2, 2016

(54) COMPUTER ASSISTED ORTHOPEDIC SURGERY SYSTEM FOR LIGAMENT RECONSTRUCTION

(75) Inventors: Philippe Didier Colombet, Bordeaux-Cauderan (FR); Stephane Lavallee, Saint Martin d'Uriage (FR); Carinne Granchi, New York, NY (US)

(73) Assignee: Perception Raisonnement Action en Medecine, La Tronche (FR)

( * ) Notice: Subject to any disclaimer, the term of this patent is extended or adjusted under 35 U.S.C. 154(b) by 1428 days.

(21) Appl. No.: 12/704,200

(22) Filed: Feb. 11, 2010

(65) Prior Publication Data

US 2010/0234770 A1    Sep. 16, 2010

Related U.S. Application Data

(63) Continuation of application No. 11/299,287, filed on Dec. 8, 2005, now abandoned.

(60) Provisional application No. 60/634,358, filed on Dec. 8, 2004.

(51) Int. Cl.
*A61B 19/00* (2006.01)
*A61B 5/06* (2006.01)
(Continued)

(52) U.S. Cl.
CPC ............. *A61B 19/5244* (2013.01); *A61B 5/064* (2013.01); *A61B 5/103* (2013.01); *A61B 5/4533* (2013.01); *A61B 17/1764* (2013.01); *A61B 19/50* (2013.01); *A61B 19/52* (2013.01); *A61B 5/6878* (2013.01); *A61B 17/1714* (2013.01); *A61B 19/56* (2013.01);
(Continued)

(58) Field of Classification Search
CPC ...... A61B 5/11; A61B 5/1121; A61B 5/1122; A61B 5/4528; A61B 2019/505
USPC .................................................. 600/587, 595
See application file for complete search history.

(56) References Cited

U.S. PATENT DOCUMENTS 5,335,674 A * 8/1994 Siegler ........................... 600/595
5,961,474 A * 10/1999 Reis ............................... 600/595
(Continued)

FOREIGN PATENT DOCUMENTS

WO    WO 0236031 A1 *  5/2002

OTHER PUBLICATIONS

Office Action issued Aug. 12, 2009 in U.S. Appl. No. 11/299,287.
(Continued)

*Primary Examiner* — Adam J Eiseman
(74) *Attorney, Agent, or Firm* — Kim Winston LLP

(57) ABSTRACT

A computer assisted orthopedic surgery system for ligament graft reconstruction includes a system for obtaining data indicative of a location for ligament graft placement with respect to at least a first bone and a second bone. The system includes a position determining device that is capable of tracking the relative movements of the first and second bones using reference bodies that are attached to the first and second bones and a pointer that has a tip for contacting a surface of at least one of the first and second bones to capture one or more reference points. The system further includes a computer that is configured to determine and track intraoperative positions of the reference bodies and the pointer and to provide isometric and impingement data for a ligament graft placement based on a realistic simulation of a trajectory of a deformable ligament graft.

18 Claims, 31 Drawing Sheets

(51) Int. Cl.
   *A61B 5/103* (2006.01)
   *A61B 5/00* (2006.01)
   *A61B 17/17* (2006.01)

(52) U.S. Cl.
   CPC .... *A61B 2019/502* (2013.01); *A61B 2019/505* (2013.01); *A61B 2019/507* (2013.01); *A61B 2019/5255* (2013.01); *A61B 2019/5268* (2013.01); *A61B 2019/5291* (2013.01); *A61B 2019/562* (2013.01); *A61B 2019/564* (2013.01)

(56) References Cited

U.S. PATENT DOCUMENTS

| | | | |
|---|---|---|---|
| 6,551,258 B1 * | 4/2003 | Herling et al. | 600/595 |
| 6,725,082 B2 * | 4/2004 | Sati et al. | 600/429 |
| 2003/0153978 A1 * | 8/2003 | Whiteside | 623/20.21 |
| 2004/0153080 A1 * | 8/2004 | Dong et al. | 606/80 |
| 2004/0254771 A1 * | 12/2004 | Riener et al. | 703/7 |
| 2005/0101966 A1 * | 5/2005 | Lavallee | 606/102 |
| 2006/0241405 A1 * | 10/2006 | Leitner et al. | 600/426 |
| 2006/0245627 A1 * | 11/2006 | Nagamune | 382/128 |

OTHER PUBLICATIONS

Fleute, Markus et al., "Incorporating a statistically based shape model into a system for computer-assisted anterior cruciate ligament surgery" Medical Image Analysis vol. 3, No. 3 pp. 209-222, (1999).

Scuderi, Giles R. et al. Classification of Knee Ligament Injuries, Surgery of the knee, pp. 585-599.

* cited by examiner

COMPUTER ASSISTED ORTHOPEDIC SURGERY SYSTEM FOR LIGAMENT RECONSTRUCTION

CROSS REFERENCE TO RELATED APPLICATION

The present application is a continuation application of U.S. patent application Ser. No. 11/299,287, filed Dec. 8, 2005 which claims the benefit of U.S. patent application Ser. No. 60/634,358, filed Dec. 8, 2004, each of which are hereby incorporated by reference in their entirety.

TECHNICAL FIELD

The present invention relates to a method and system for computerized ligament reconstruction surgery.

BACKGROUND

Injury to the anterior cruciate ligament (ACL) is the most common ligament injury in the knee, resulting in approximately 50,000 reconstructions per year in the United States (Frank: C B, Jackson D W, The Science of reconstruction of the anterior cruciate ligament. J Bone Joint Surg. Am 79: 1556, 1997). Unfortunately, approximately 40% of ACL ligaments are improperly misplaced in surgery, which can result in post-operative knee instability, abnormal kinematics, and premature degeneration of structures.

Misplacements in knee surgery are common because ligament reconstruction is a technically challenging procedure for the surgeon. The knee joint complex is interconnected with several structural ligaments and surrounding tissues, which may or may not be functioning normally at the time of surgery.

Trauma related injuries which cause ACL rupture often entail damage to other structures surrounding the knee joint, such as the medial or the lateral collateral ligaments. Additionally, posterior cruciate ligament (PCL) ruptures or tears can occur and require diagnosis and/or surgical reconstruction. These surrounding structures are also critical for insuring adequate knee function, rotatory stability, and normal kinematics.

Although various clinical tests for assessing knee instability exist, it is extremely difficult for the surgeon to objectively take these results into consideration when determining the optimal course of a ligament graft. In particular, the magnitudes and directions of the laxities and their interrelationships to the underlying anatomical structures can be elusive, with the combined translational and rotational motions of the knee joint. Moreover, these interrelationships may change over the course of the surgery as structures are removed and/or reconstructed.

One method for determining the femoral point of graft attachment during ACL replacement is disclosed in European Patent Application No. 0603089 to Cinquin et al., which is hereby incorporated by reference in its entirety. The disclosed method concerns the determination of a femoral point of graft attachment with respect to a tibial graft attachment point such that the distance between these two points remains invariant during knee flexion and extension. The positions within an on-site three-dimensional coordinate system of a reference and a pointer, which are both provided with energy emitting markers, are determined by means of a three-dimensional position measurement system, such as the OPTOTRAK position measurement system, Northern Digital, Waterloo, On. The position measurement system measures the position of the markers with respect to the on-site three-dimensional coordinate system. Therewith, the position of the tip of the pointer is determinable by means of a computer.

The Cinquin method includes the steps of (1) attachment of a first reference at the tibia; (2) positioning of the pointer tip at a previously determined point T1 and measuring the position of the pointer tip with respect to the first reference; (3) positioning of the pointer tip at several points P1 at the trochlea of the femur close to that position where the invariant point is expected; (4) calculation of the distances of point T1 and each of the points P1; (5) displacement of the femur with respect to the tibia and calculation of the variations of the distances between T1 and each of the points P1; and (6) selection of that point P1 among points P1 which shows the most invariant distance.

The Cinquin method assumes that the optimal placement of a graft is determined by a simple isometric elongation criterion which relies on the ligament trajectory following the course of a straight line (i.e. the trajectory is not dependent on the intrusion of the bone surfaces nor the ligament thickness).

Ligament grafts in reality are complex structures that have an appreciable thickness (e.g., 8-10 mm in diameter), which can affect their function and geometry during joint motion. In particular, the course of these ligament bundles is often guided by the curved protruding surfaces on the ends of the femur and on the tibia in the vicinity of the ligament attachment sites. Indeed, the collateral and posterior structures of the knee are known to wrap around the curved bone surfaces of the femur and tibia which can influence the ligament trajectory and elongation patterns during knee motion. As a result, a linear based determination of the isometric elongation characteristics of the ligament is too simplistic and does not account for the realities of a typical operative site where the ligament does not follow a purely linear path.

Another disadvantage of the Cinquin method is that only a normal flexion extension motion of the knee joint kinematics is considered in the determination of the fixation point of the ligament graft, and no consideration is taken for the surrounding structures and their associated laxities.

U.S. Pat. No. 6,725,082 (which is hereby incorporated by reference in its entirety) discloses an image-based system and method for computer-assisted ACL replacement in which landmark points are identified on the bones and on medical images of the knee (such as X rays, CT or MRI scans), the images are then registered to the patient, and a drilling tool is then navigated with respect to some "anatomical" graft placement criterion as determined on the medical images. This permits visualisation of the graft fixation points on the bones in the X-ray images, and in relation to the landmark points identified on the images. The disadvantage of this system is that no information or measurements regarding knee motion or laxity is provided. Furthermore, no means are provided for simulating realistic ligament trajectories based on the 3D shapes of the bones and of the ligament geometry such as the graft thickness and length.

Yet another disadvantage of conventional computer positioning systems, such as those described above, is that these systems are based almost entirely on determining optimal isometric coordinate points or locations for determining a fixation point on the femur and a fixation point on the tibia. However, there are a number of other considerations that should or can be taken into account when determining the optimal location of the ligament and for assisting the physician in selecting the appropriate procedure that is to be performed on the patient. For example, knee laxity data can assist the physician in determining the type of procedure to be undertaken; however, this type of data is not utilized in the conventional computer systems, which again, merely utilize isometric data to model a straight line (linear) layout for the ligament.

SUMMARY

The present invention relates to a system for reconstructing ligaments that connect to at least two bones. The invention aids the surgeon in determining the course of a replacement ligament by taking into consideration the laxities of the involved joint, as well as the geometric properties of the ligament graft, and the impingement of the bones onto the graft.

In one aspect of the invention, a computer-assisted orthopedic surgery (CAOS) system is provided and is configured for performing ligament reconstruction procedures on a patient, such as those performed in knee surgery. The system includes a position measurement device in communication with a computer to determine the position and orientation of objects in a three dimensional coordinate system. The three dimensional coordinate system includes at least one bone, such as the patient's femur or tibia. Objects to be tracked comprise at least three markers (or triplets), which can be configured to emit, receive, or reflect energy, such as light or acoustic energy.

To sense the position of light reflecting markers, the system includes at least two detecting elements, such as two cameras. The two cameras detect the light reflected from the light reflecting markers to determine the position of each marker associated with an object to be tracked. Based on the respective positions of markers associated with the tracked object, the position and orientation of the tracked object are determined.

The system preferably includes a plurality of reference bodies that can be used to determine the position and orientation of a patient's bone. The reference bodies can be rigid members having at least three markers each. Each reference body preferably includes an attachment element, such as a screw or pin, with which the reference bodies can be attached to a bone. For example, respective reference bodies can be attached to the femur and tibia.

The system also can include a pointer. The pointer includes markers that allow the position and orientation of the pointer to be determined. The system also includes a calibration device that can be used to measure the relationship between the pointer tip and the markers. Thus, the position of the pointer tip can be determined from the positions of the markers relative to the three-dimensional coordinate system.

The computer can be configured to determine the position and orientation of the reference bodies and pointer based upon the position and orientation of the associated markers.

Moreover, the system can be configured for identifying and applying an anatomical coordinate system to at least two bones of the joint. The anatomical coordinate system can include directions such as medial-lateral, proximal-distal, anterior-posterior, and so on.

In a further aspect, the present invention can provide a system for determining intra-operatively the three dimensional shape of the bone surface in the vicinity of the articulating joint and in particular in the vicinity of the ligament graft fixation points associated with the joint. In particular, the three dimensional shapes of the involved bones may be provided with image free techniques.

In another aspect, the present invention can provide a system for passively guiding the manipulation of a first bone relative to a second bone, in relation to a predetermined anatomical coordinate system. In particular, these passive motions include translational and rotational displacements in directions "abnormal" to the primary functional motion of the joint (e.g. axial rotation of the knee), in addition to "normal" rotations about the primary functional axes of the joint (e.g. knee flexion). Examples of such kinematic protocols can be found in Scuderi G R. Scott N W, Classification of Knee Ligament Injuries In Insall Scott (Eds.) Surgery of the Knee, Chapter 29, pp. 585-599. In addition, joint angles can be determined and displayed in real time during the passive manipulations (e.g. flexion angle=20°).

In still another aspect, the present invention can provide a system for measuring the relative motion of one bone with respect to another bone, and for projecting the measured trajectories and amplitudes of motion of various points onto various planes and directions in relation to a predetermined anatomical coordinate system. For example, to evaluate translational or rotational stability the trajectories of the medial and lateral tibial plateau points can be measured and displayed in relation to the femur during the kinematic acquisition. The maximum amplitude of displacement with respect to the femur of each point can then be calculated. These results can then be summarized as displacement magnitudes, or as components in a particular direction of the anatomical coordinate system, such as in the anterior-posterior direction.

And in yet another aspect, the present invention can provide a system that displays numerically and graphically on a screen the patterns, the amplitudes, and the projections of the measured trajectories.

Also in another aspect, the present invention can provide a system that displays graphically in real time a deformable and bendable model of the ligament graft superimposed on three dimensional representations of the involved bones.

In yet another aspect, the present invention can provide a method for displaying graphically isometric and impingement data superimposed on three dimensional representations of the involved bones.

Still further, the present invention can provide a system for displaying in real time the position and orientation of a surgical drilling tool in relation to the targeted graft tunnel position and orientation.

According to one embodiment, a computer assisted orthopedic surgery system for ligament graft reconstruction includes a system for obtaining data indicative of a location for ligament graft placement with respect to at least a first bone and a second bone. The system includes a position determining device that is capable of tracking the relative movements of the first and second bones using reference bodies that are attached to the first and second bones and a pointer that has a tip for contacting a surface of at least one of the first and second bones to capture one or more reference points. The system further includes a computer that is configured to determine and track intraoperative positions of the reference bodies and the pointer and to provide isometric and impingement data for a ligament graft placement based on a realistic simulation of a trajectory of a deformable ligament graft.

These and other features and aspects of the invention can be appreciated from the accompanying figures and the following description.

BRIEF DESCRIPTION OF THE DRAWING FIGURES

The foregoing and other features of the present invention will be more readily apparent from the following detailed description and drawing figures of illustrative embodiments of the invention in which.

Figure 5:
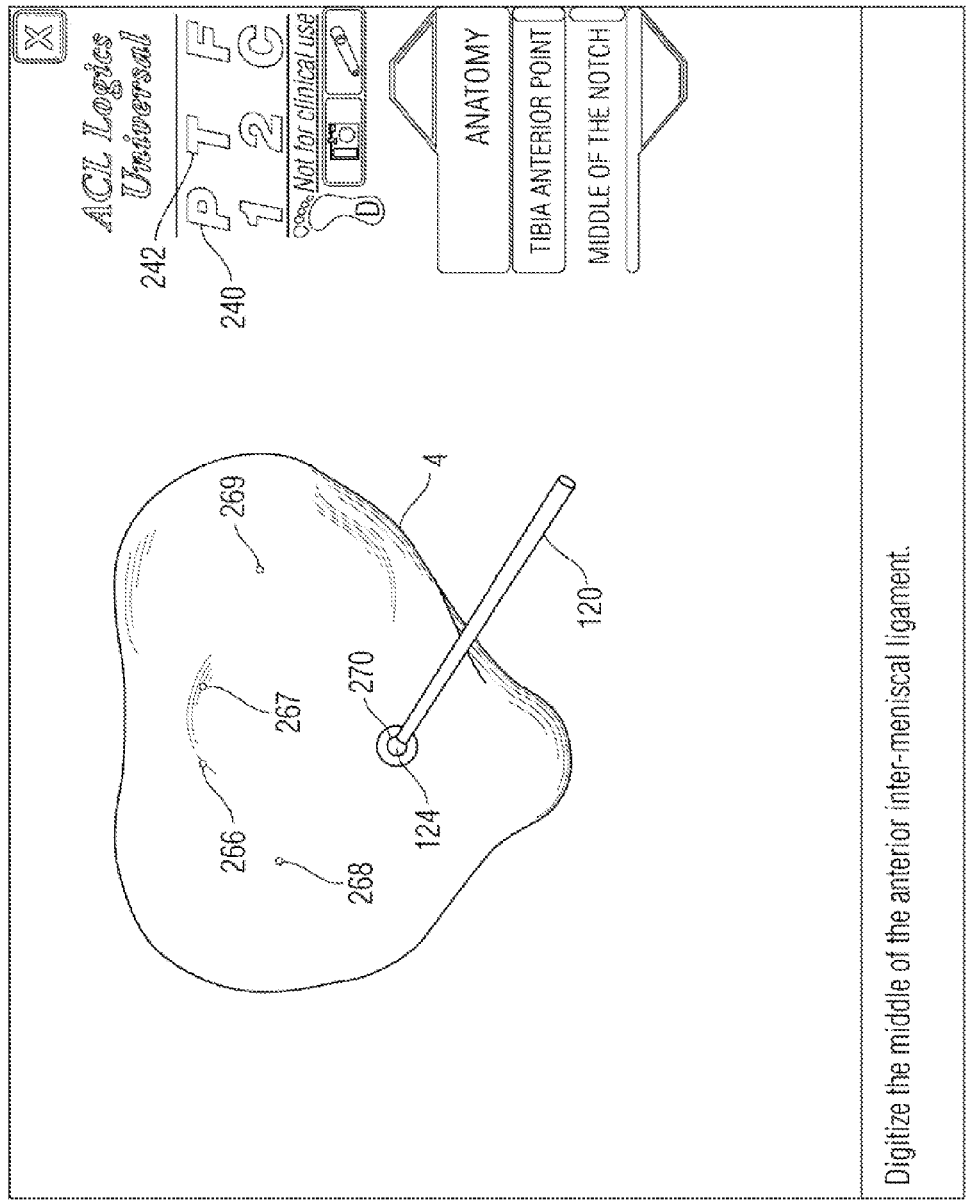
Figure 6:
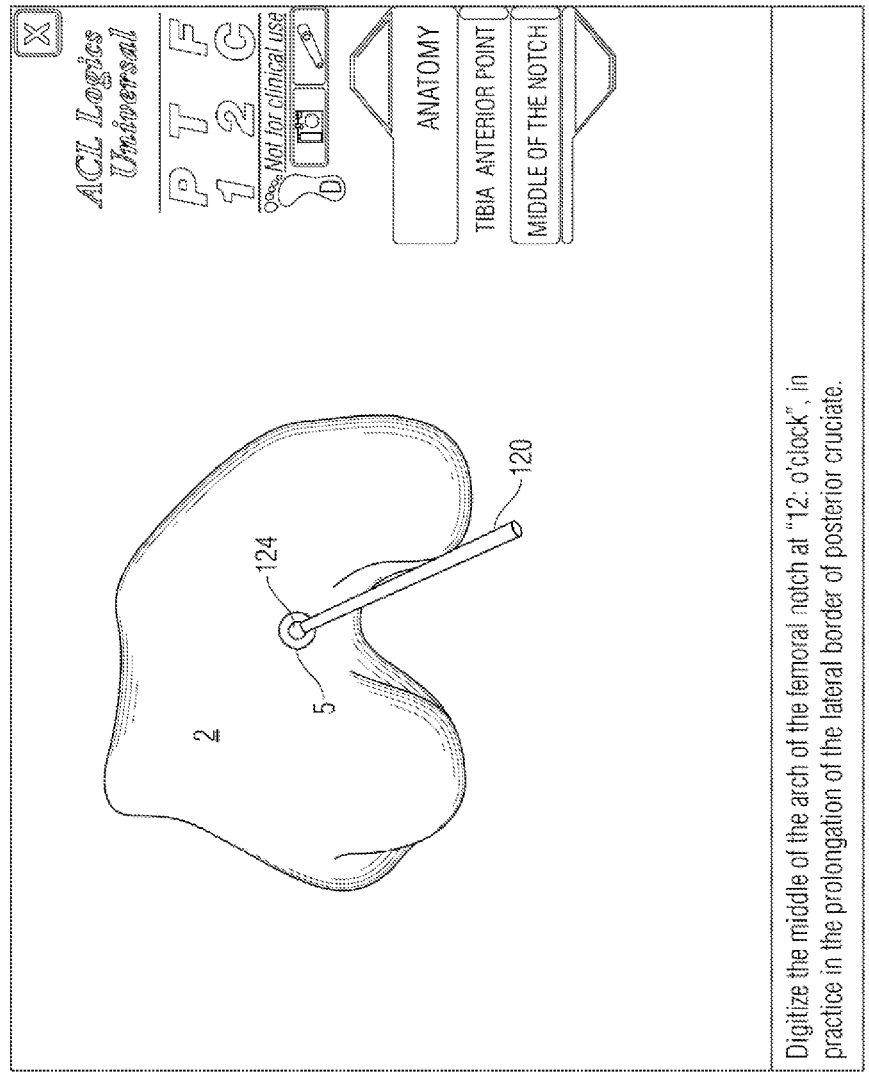
Figure 7:
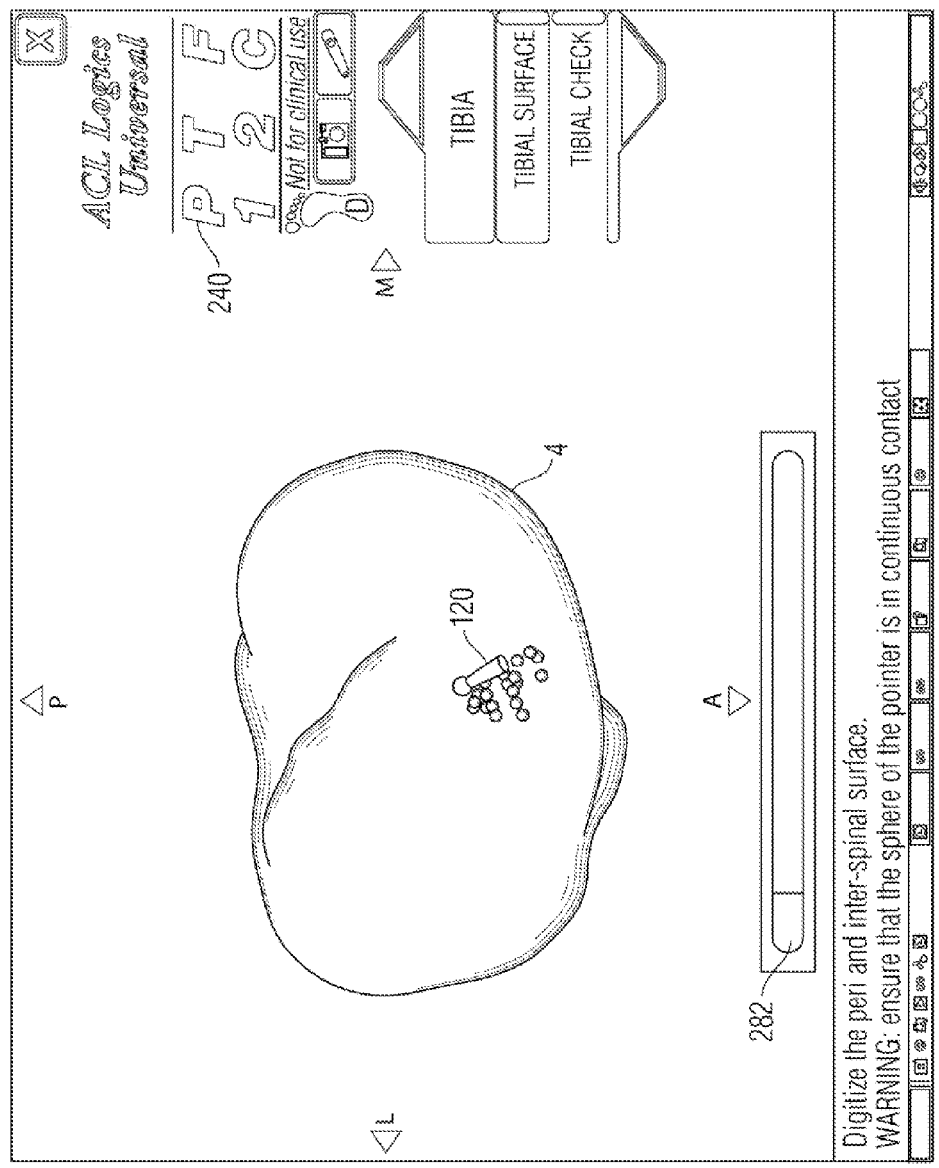
Figure 8:
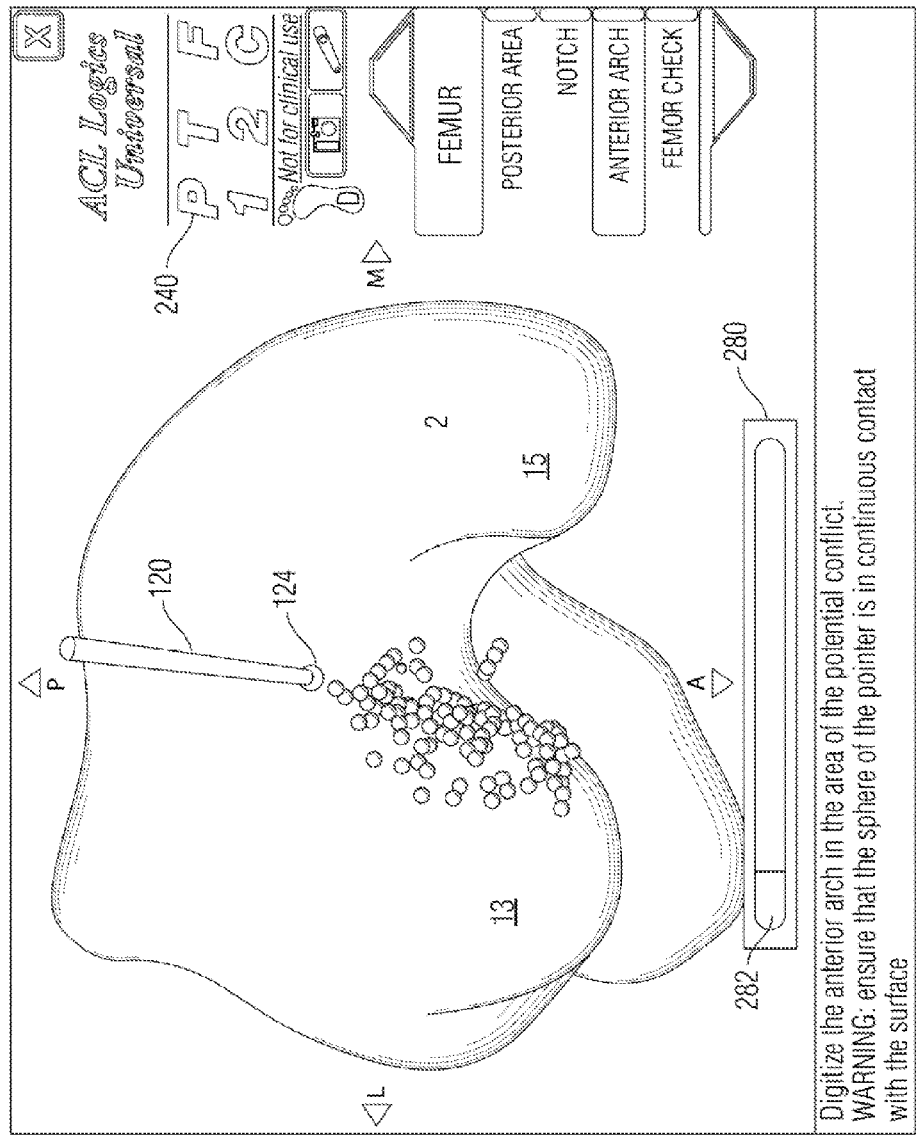
Figure 9:
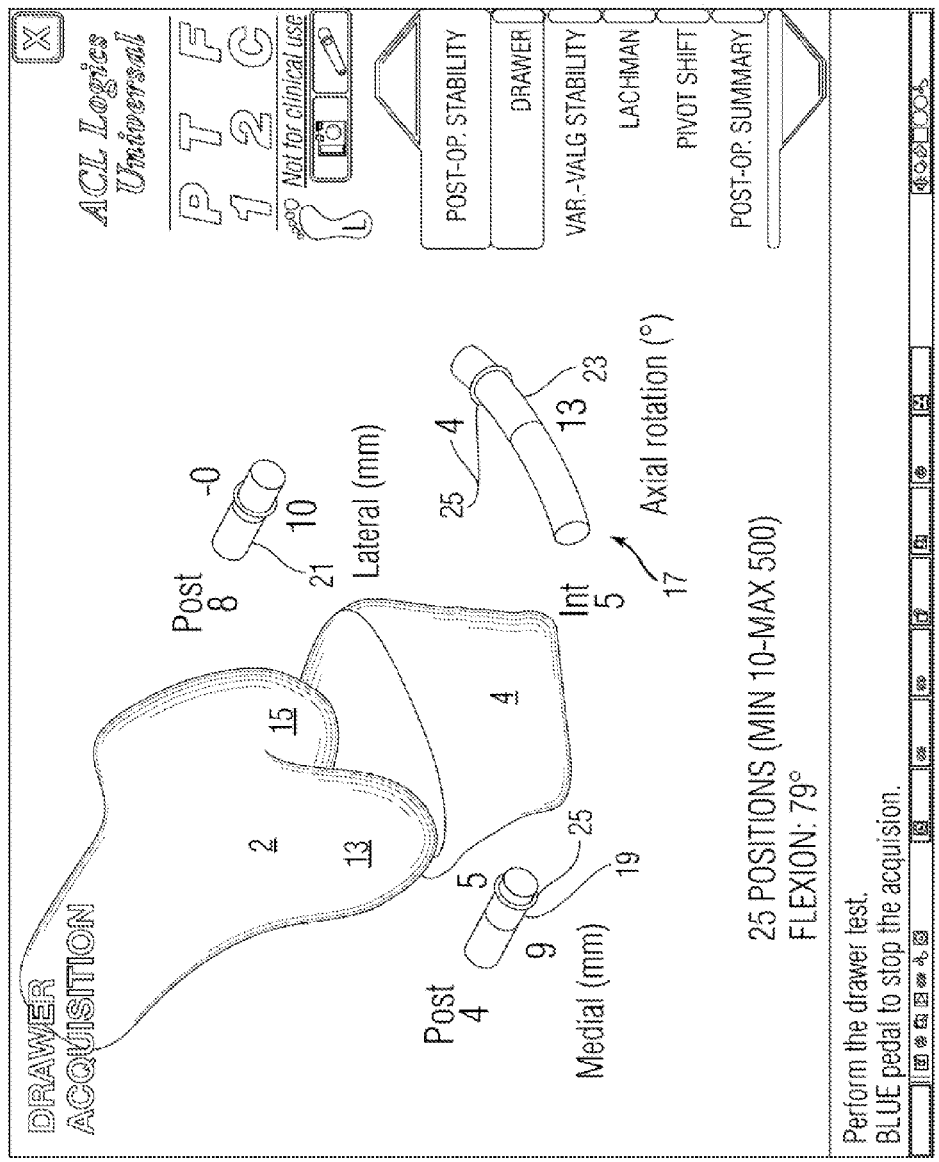
Figure 10:
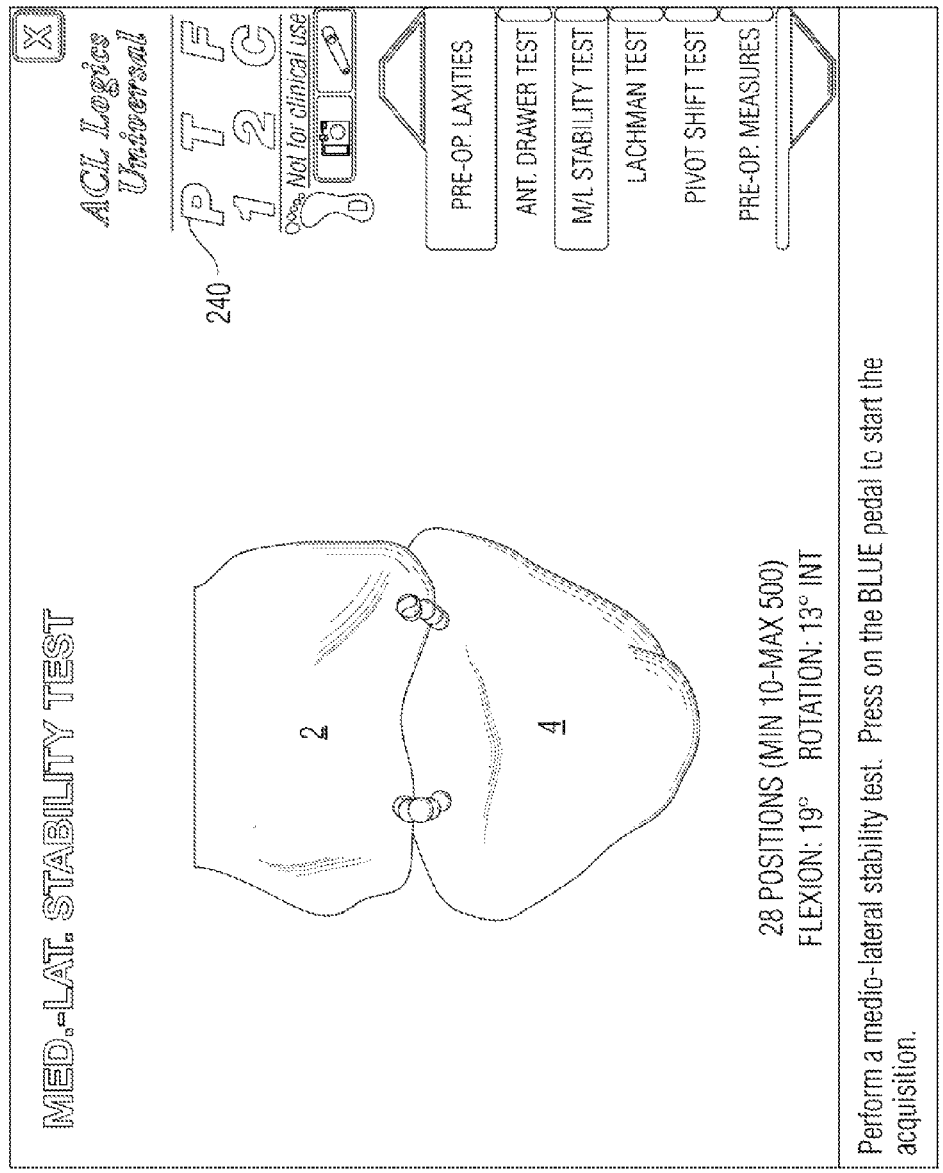
Figure 11:
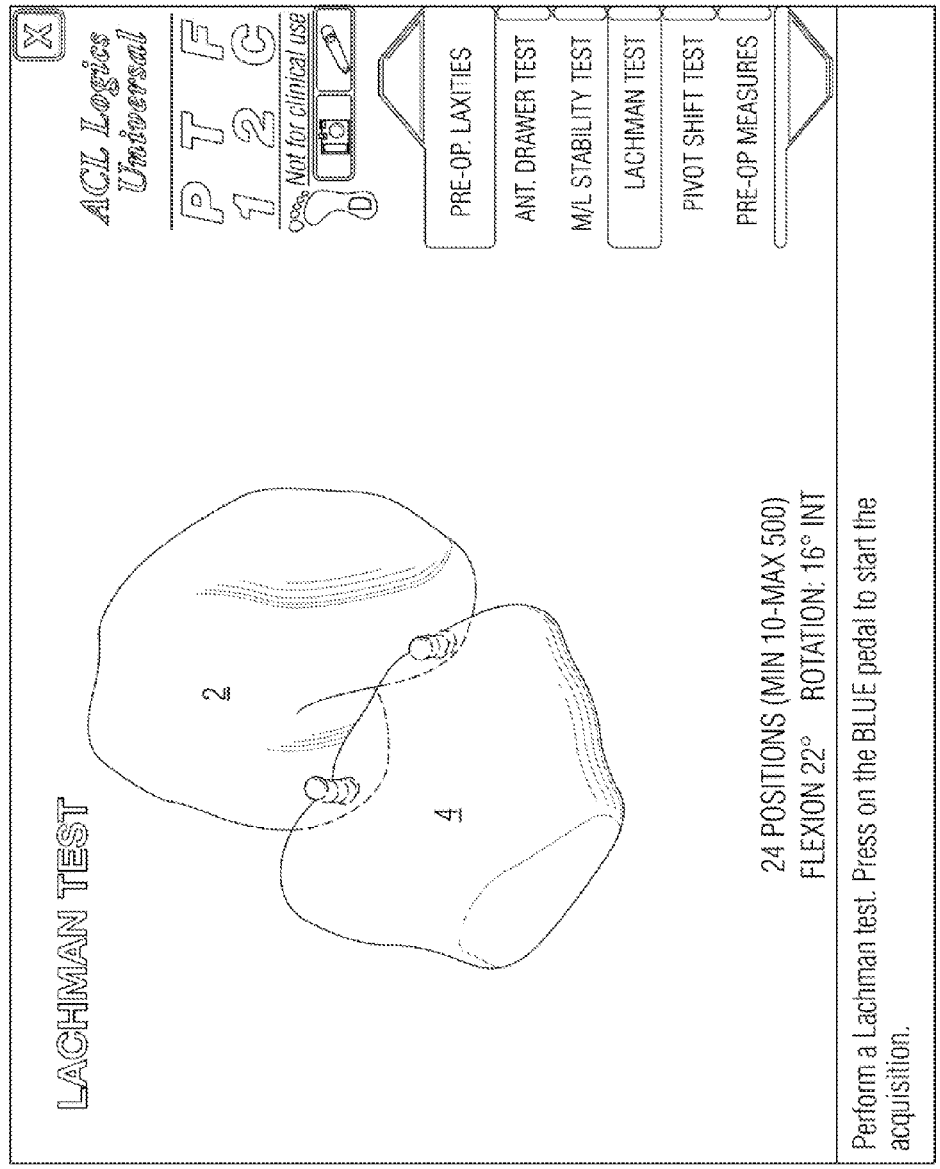
Figure 12:
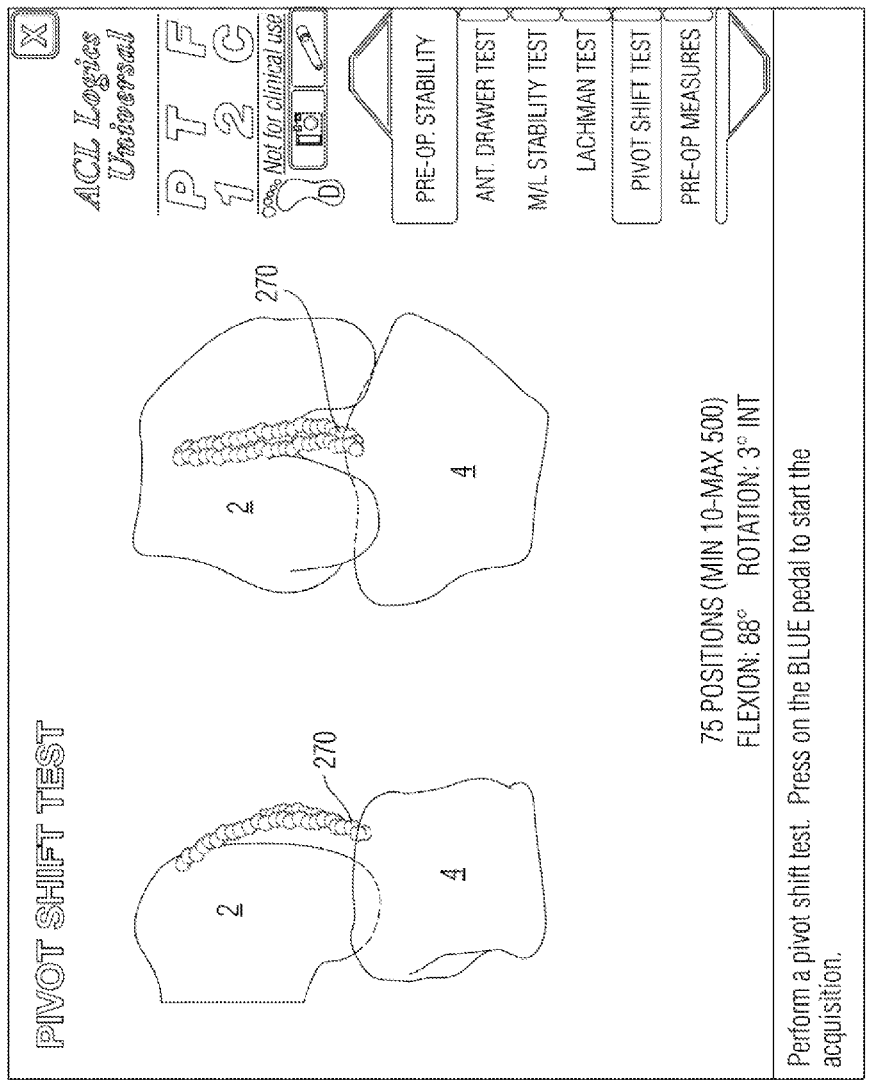
Figure 13:
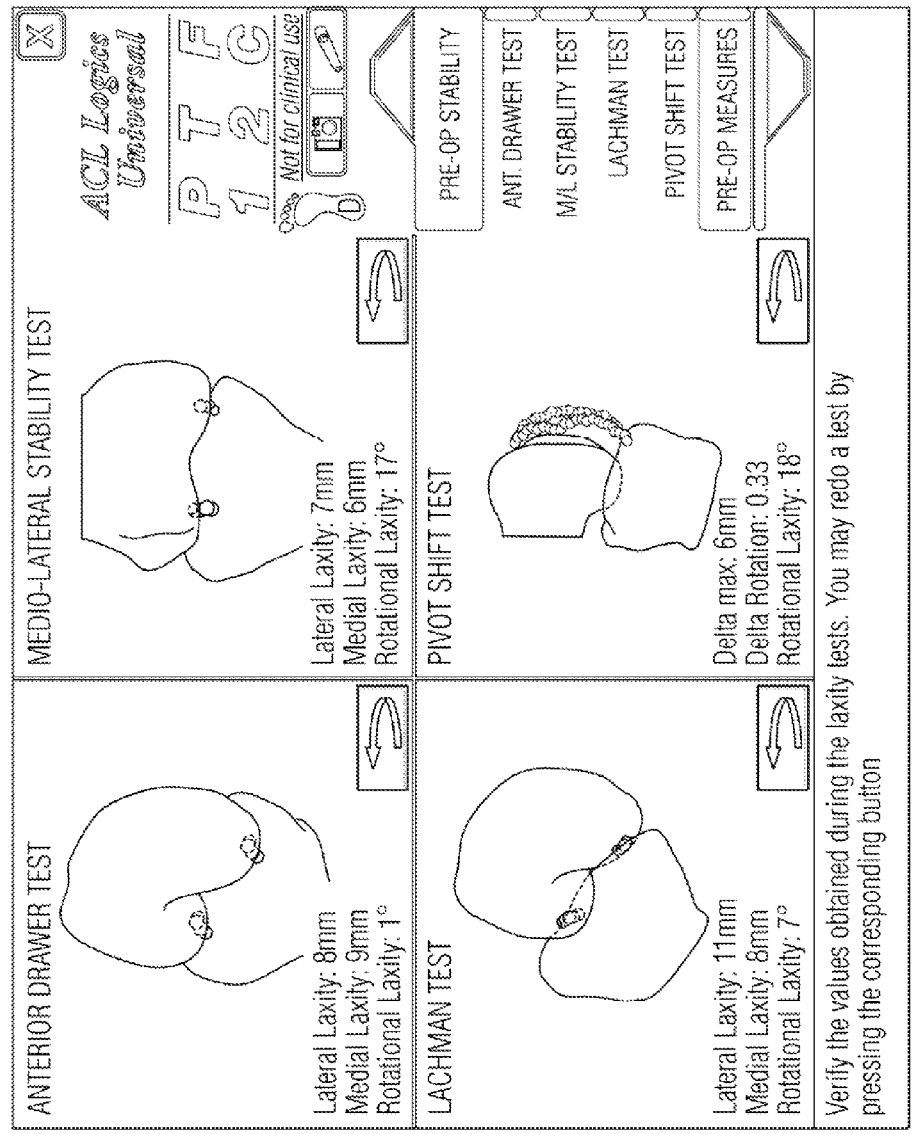
Figure 14:
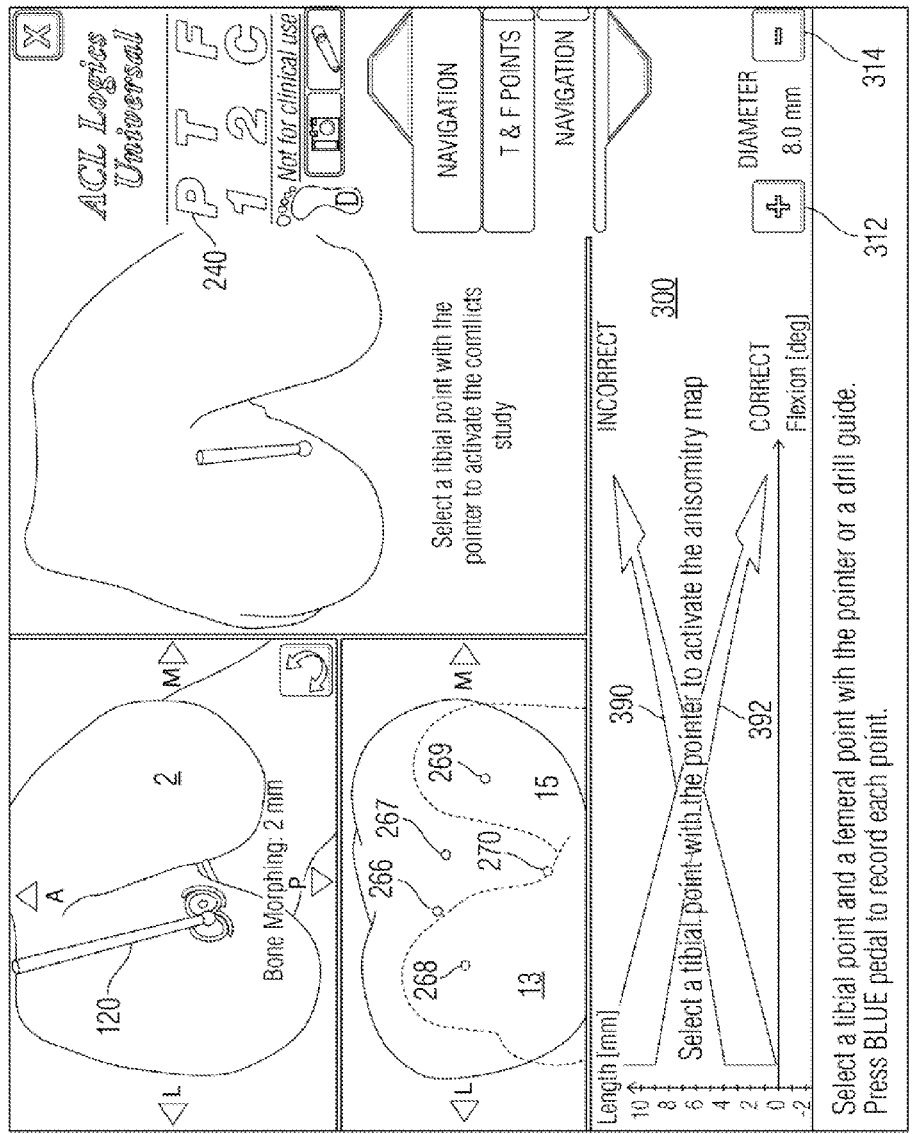
Figure 15:
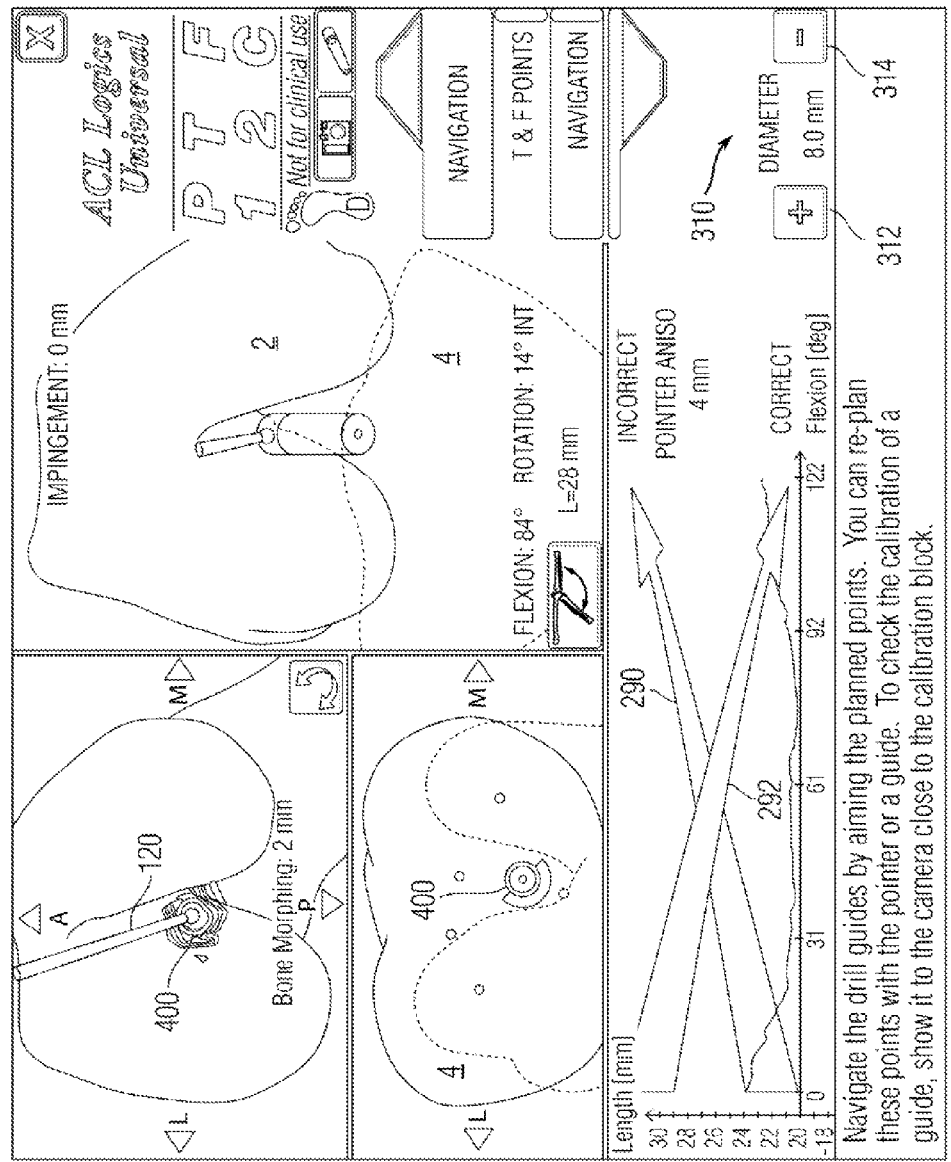
Figure 16:
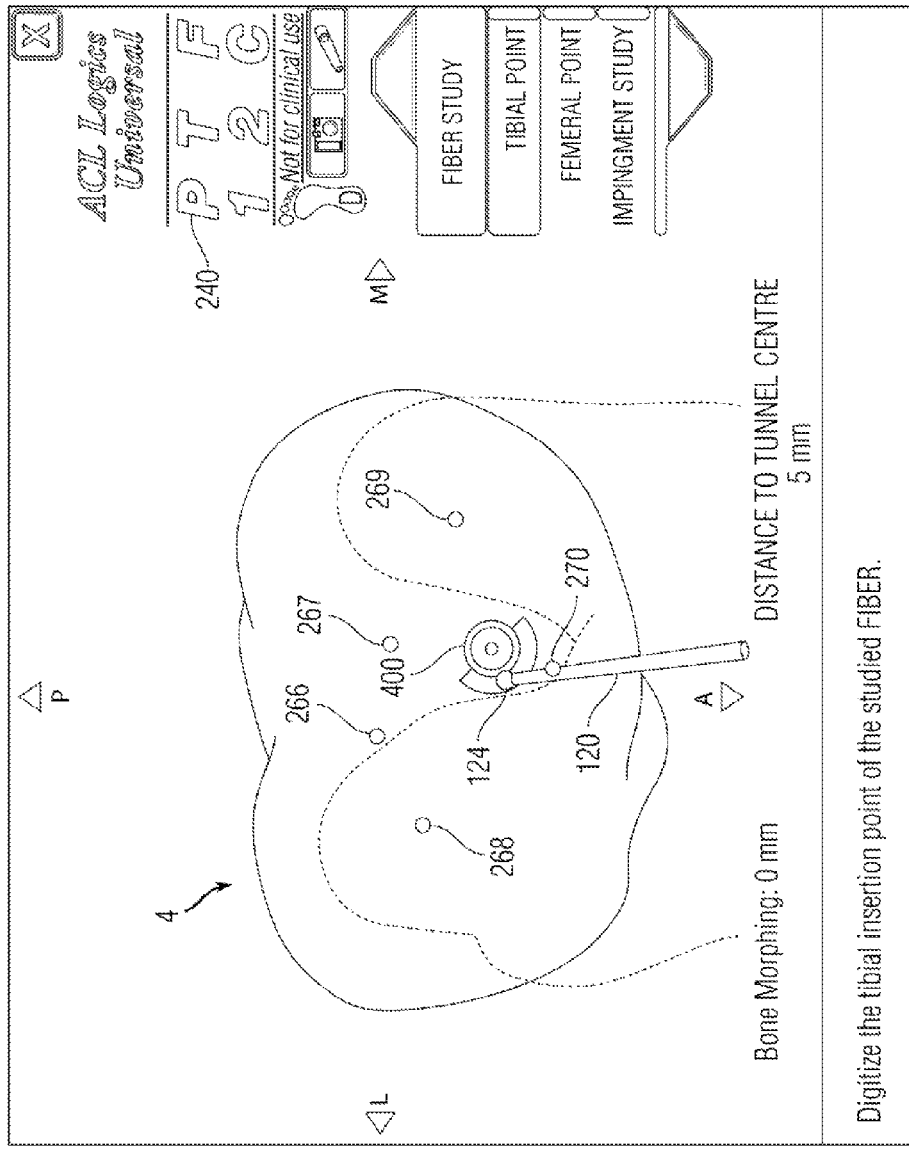
Figure 17:
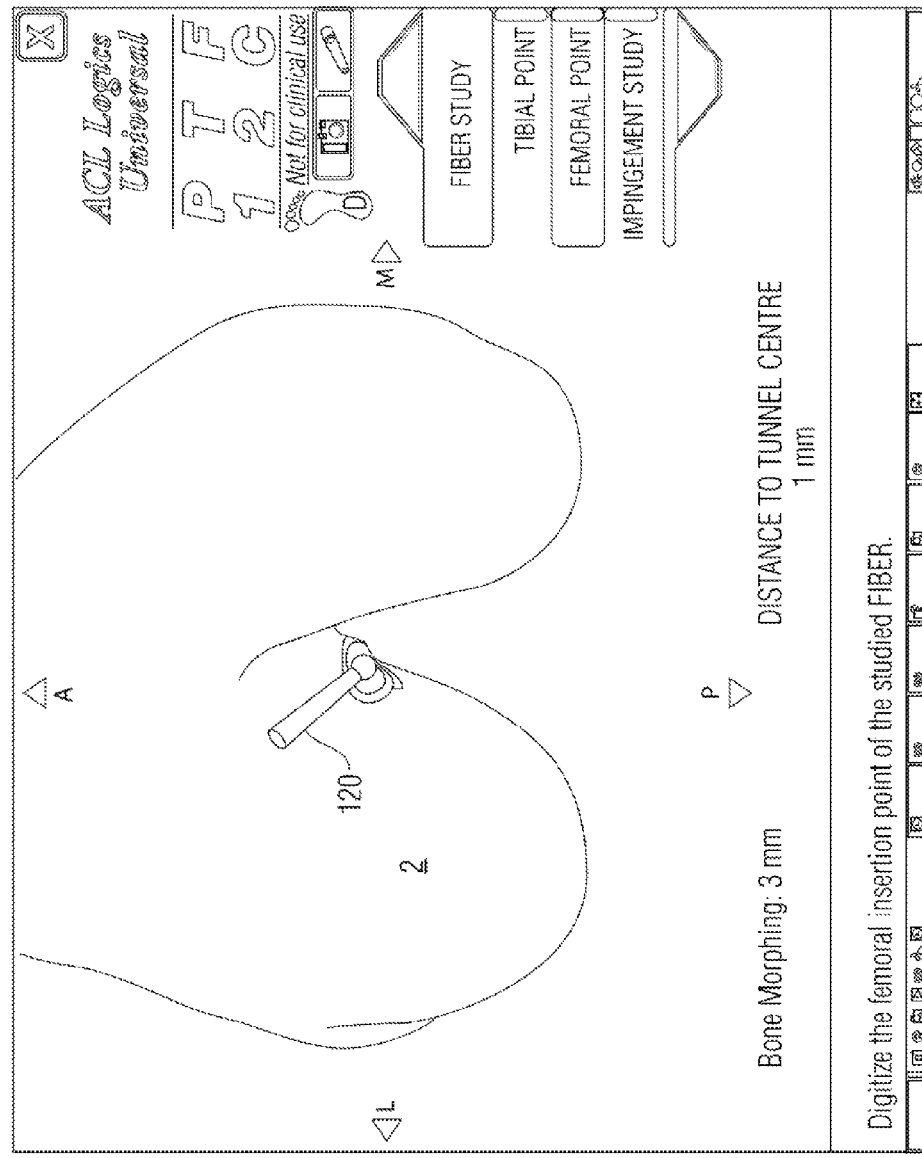
Figure 18:
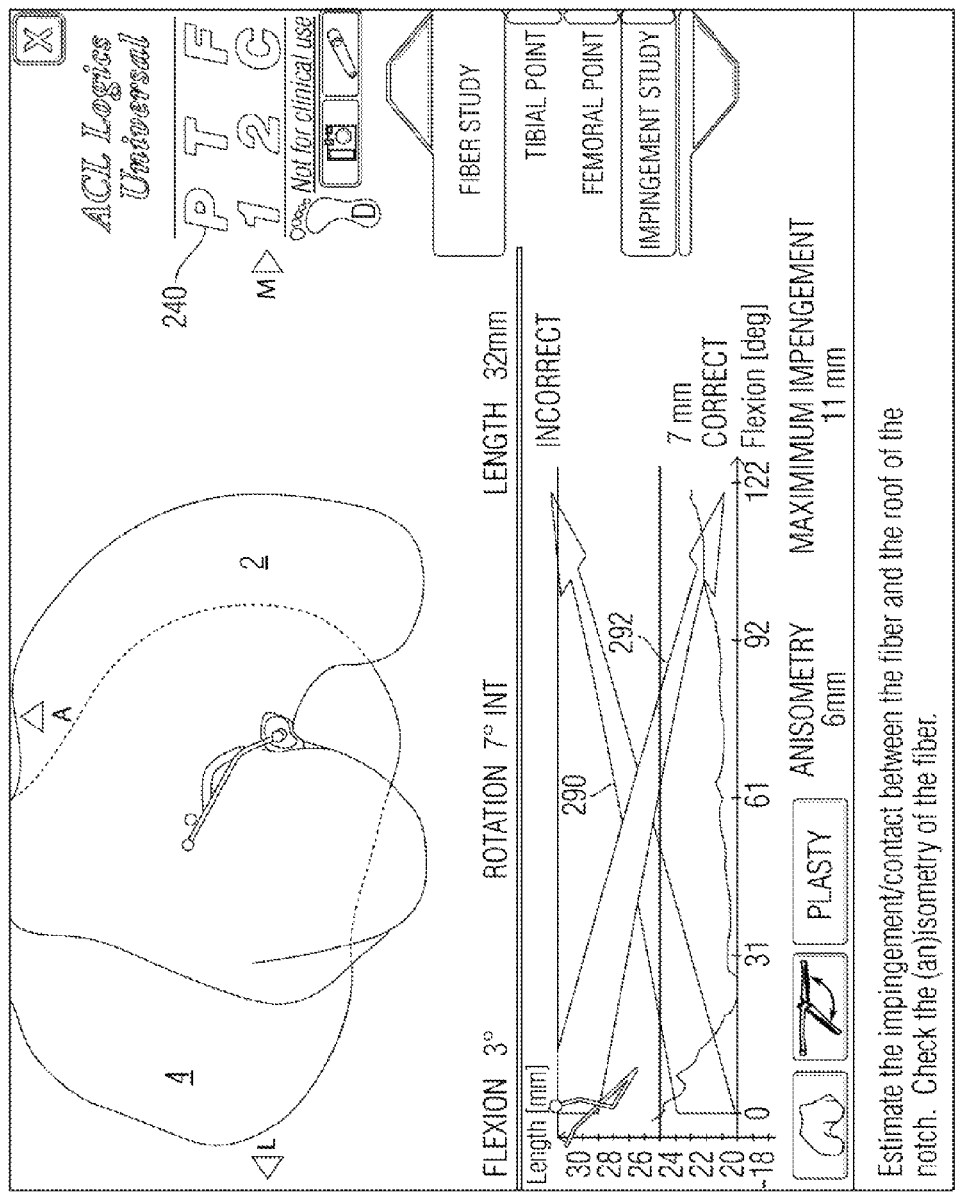
Figure 19:
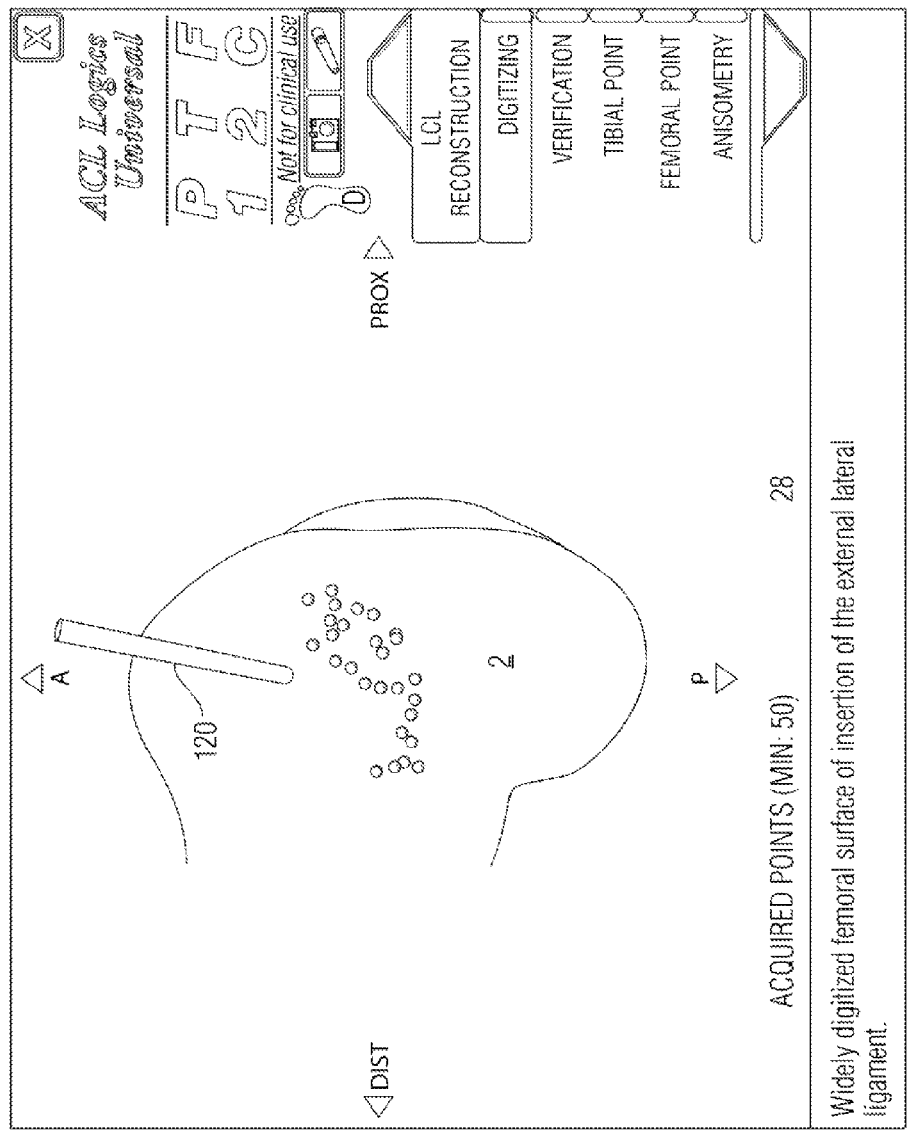
Figure 20:
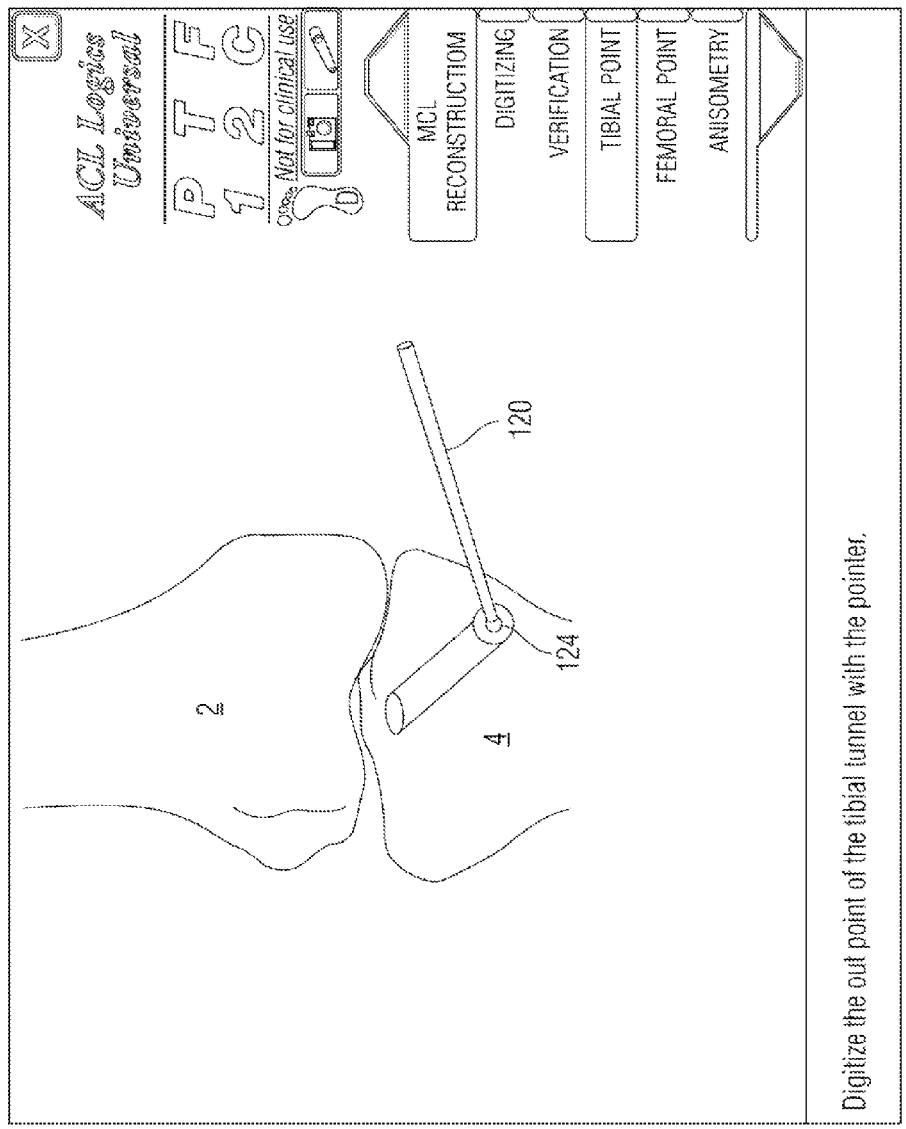
Figure 21:
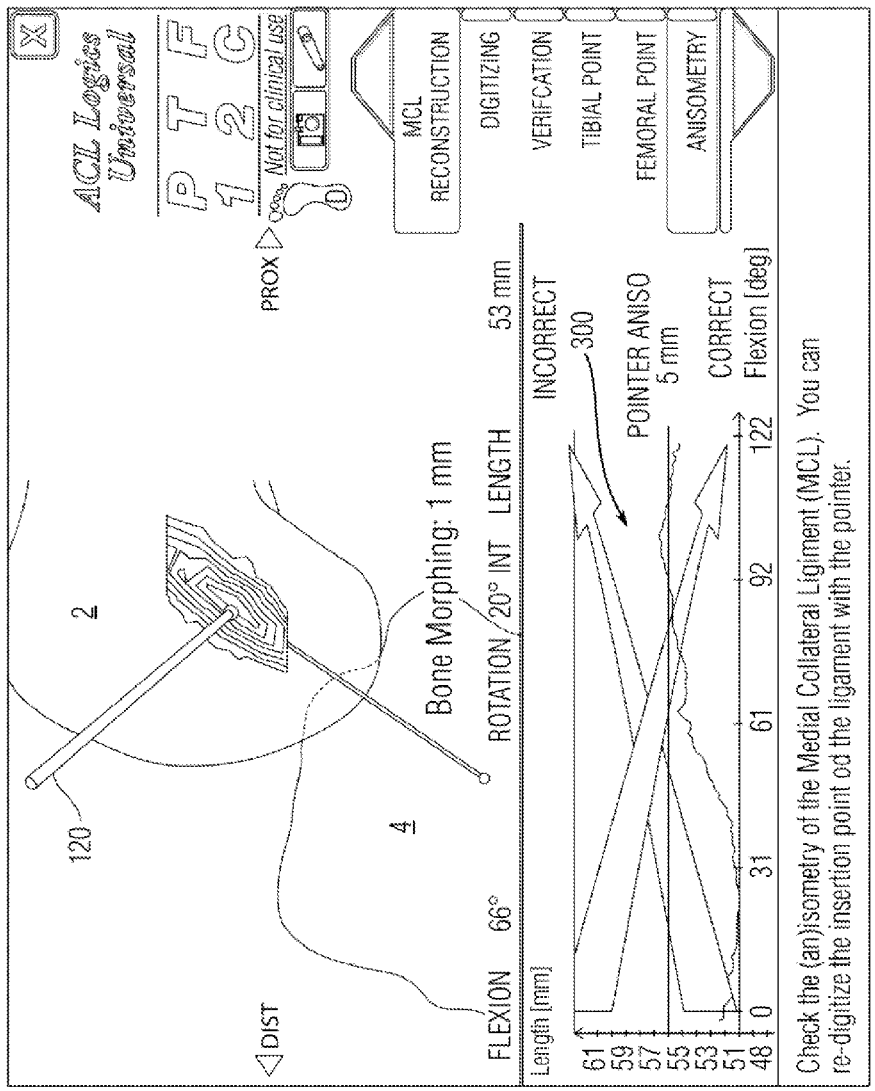
Figure 22:
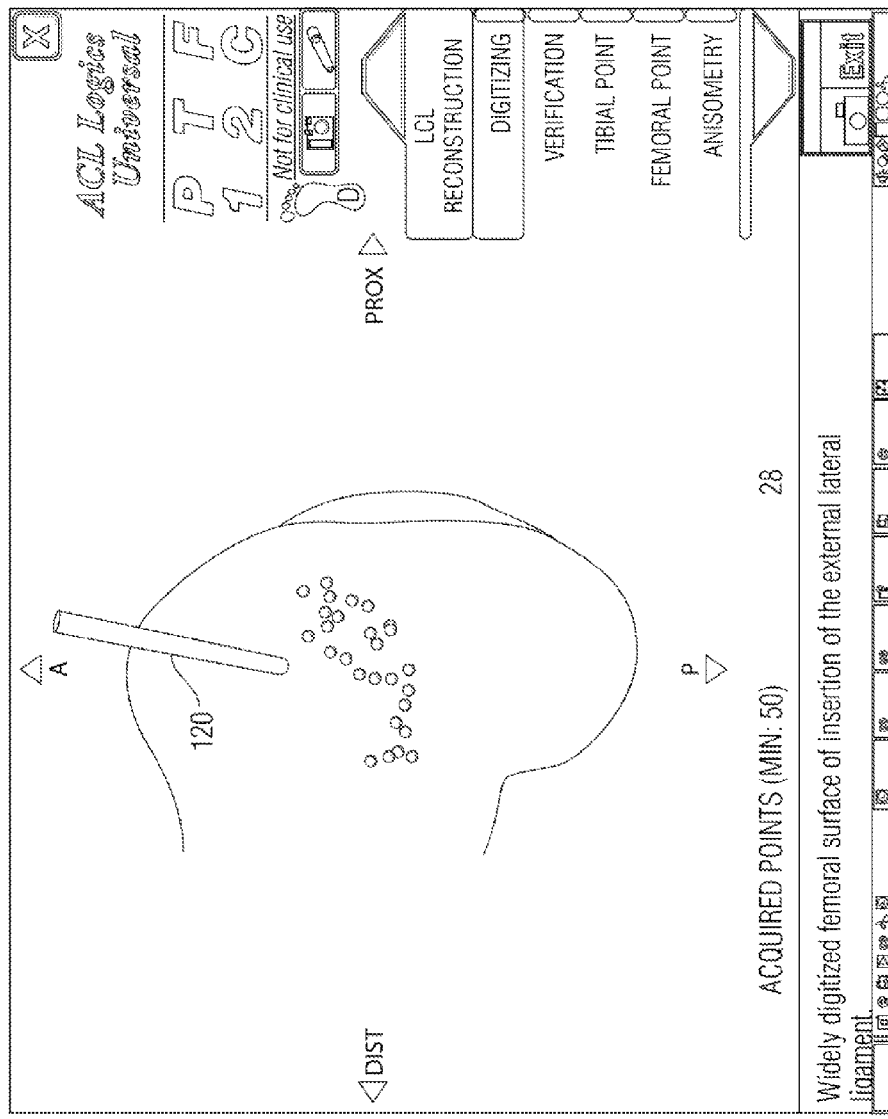
Figure 23:
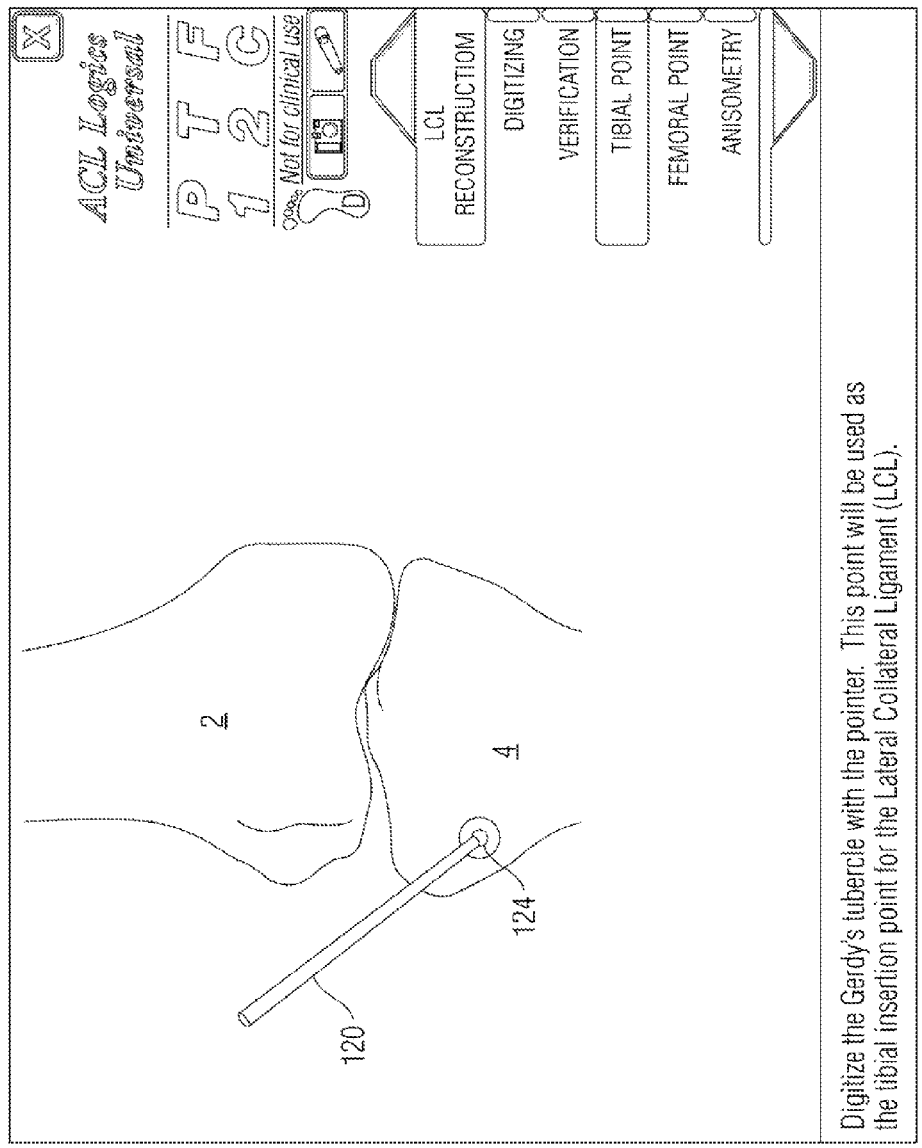
Figure 24:
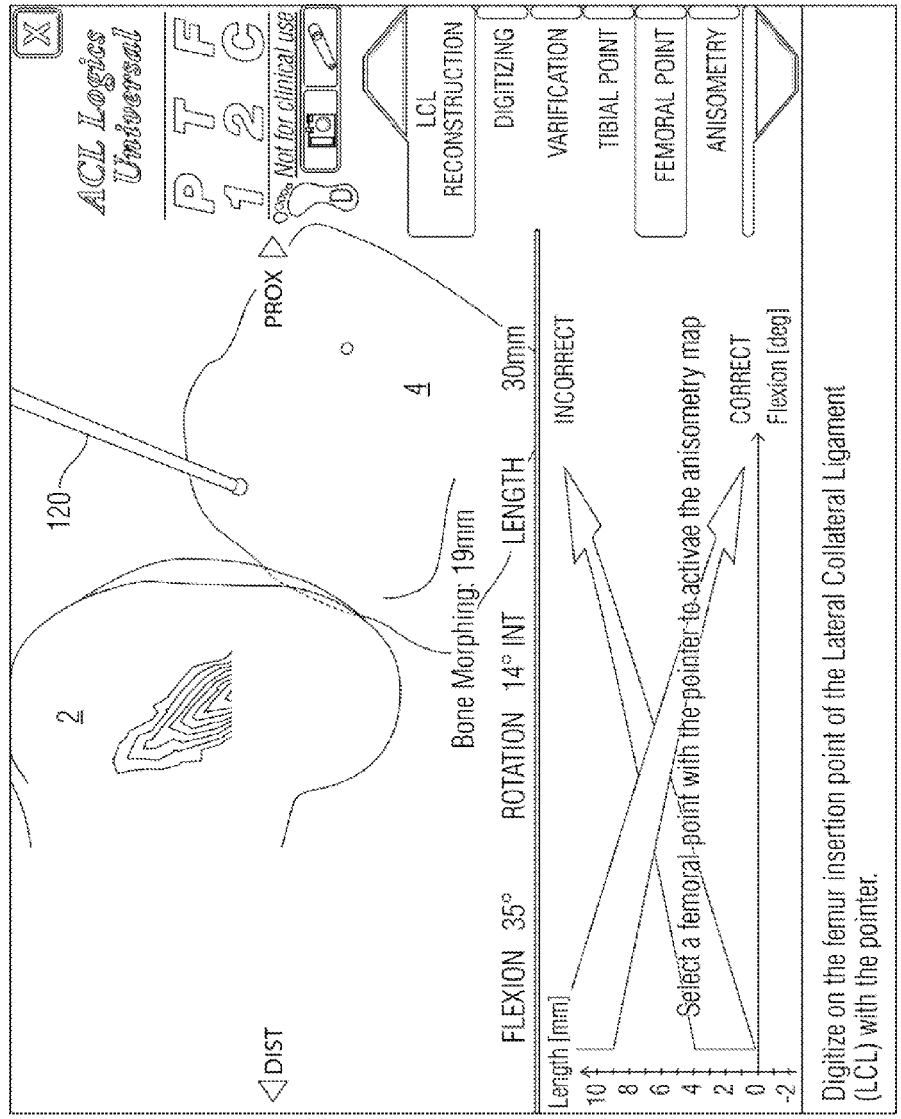
Figure 25:
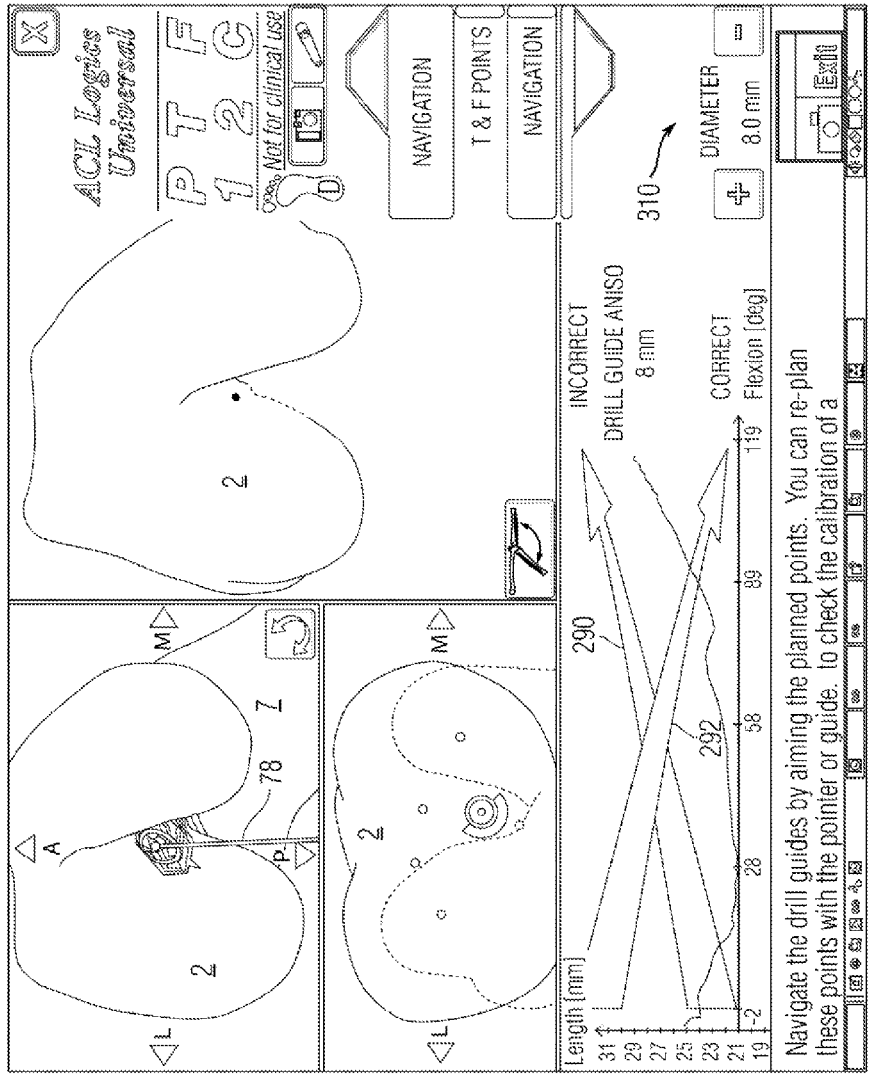
Figure 26:
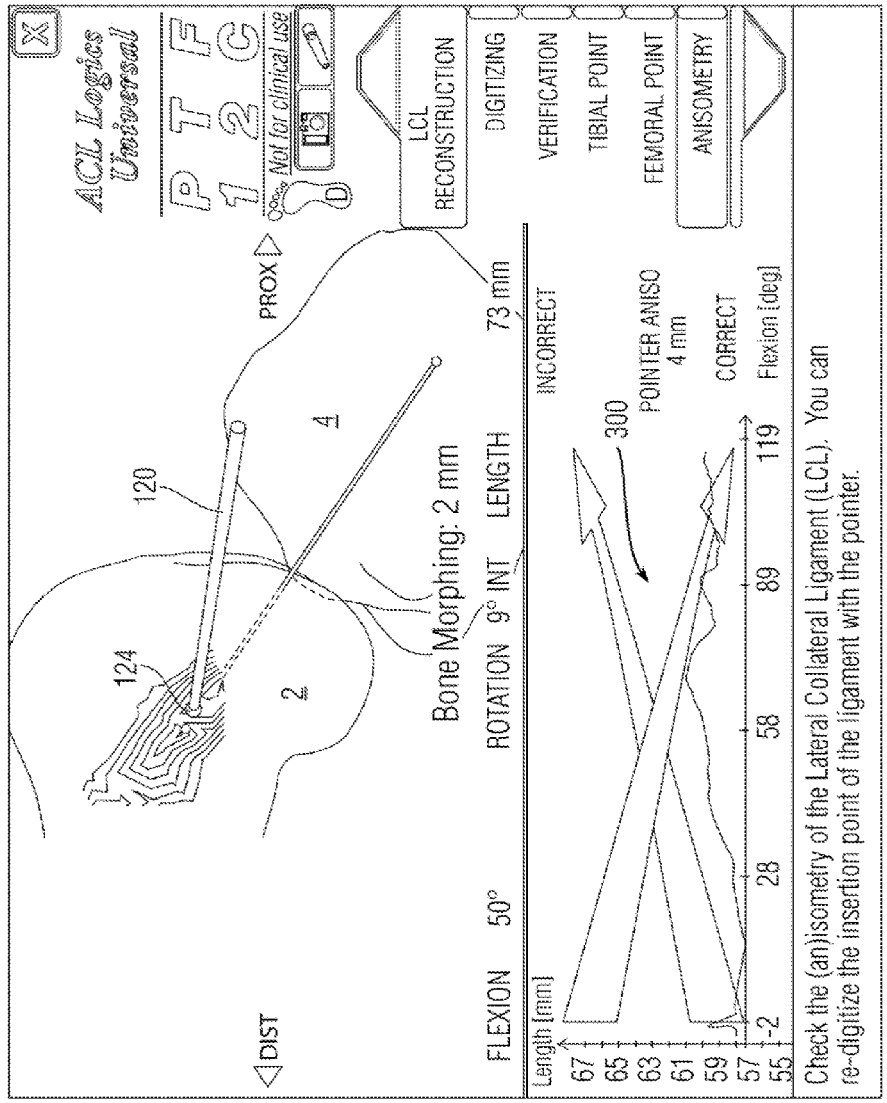
Figure 27:
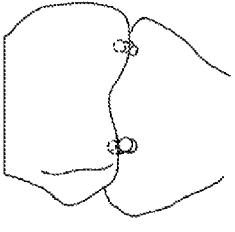
Figure 28:
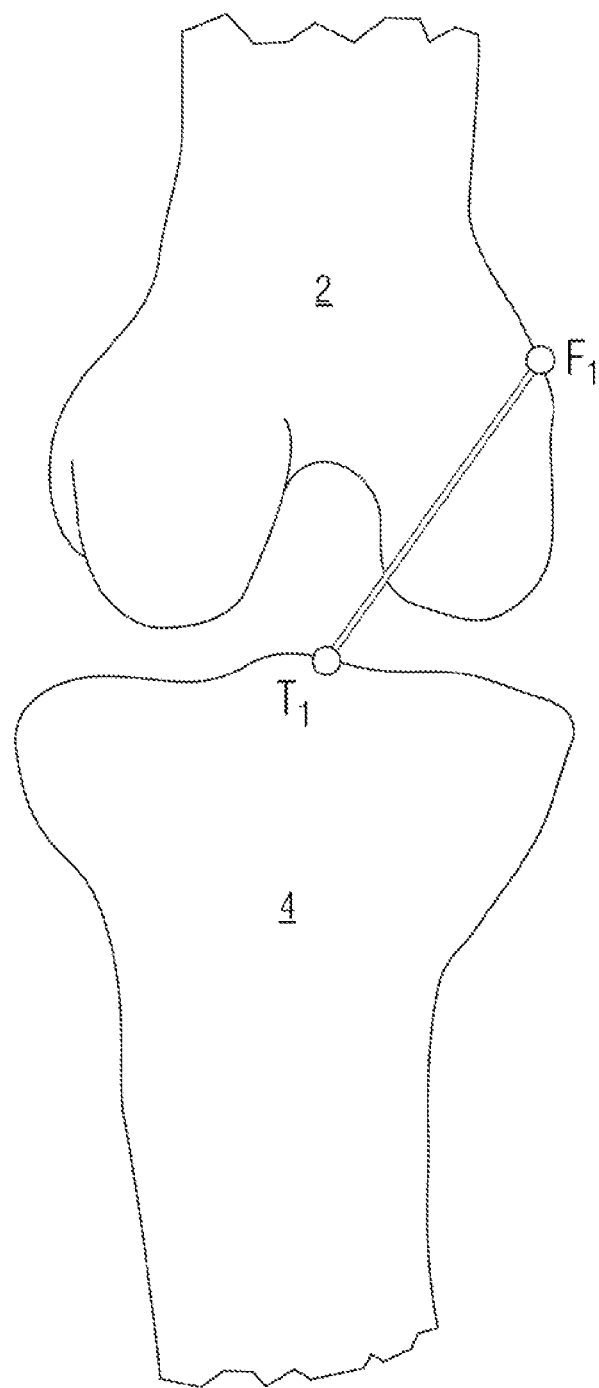
Figure 29:
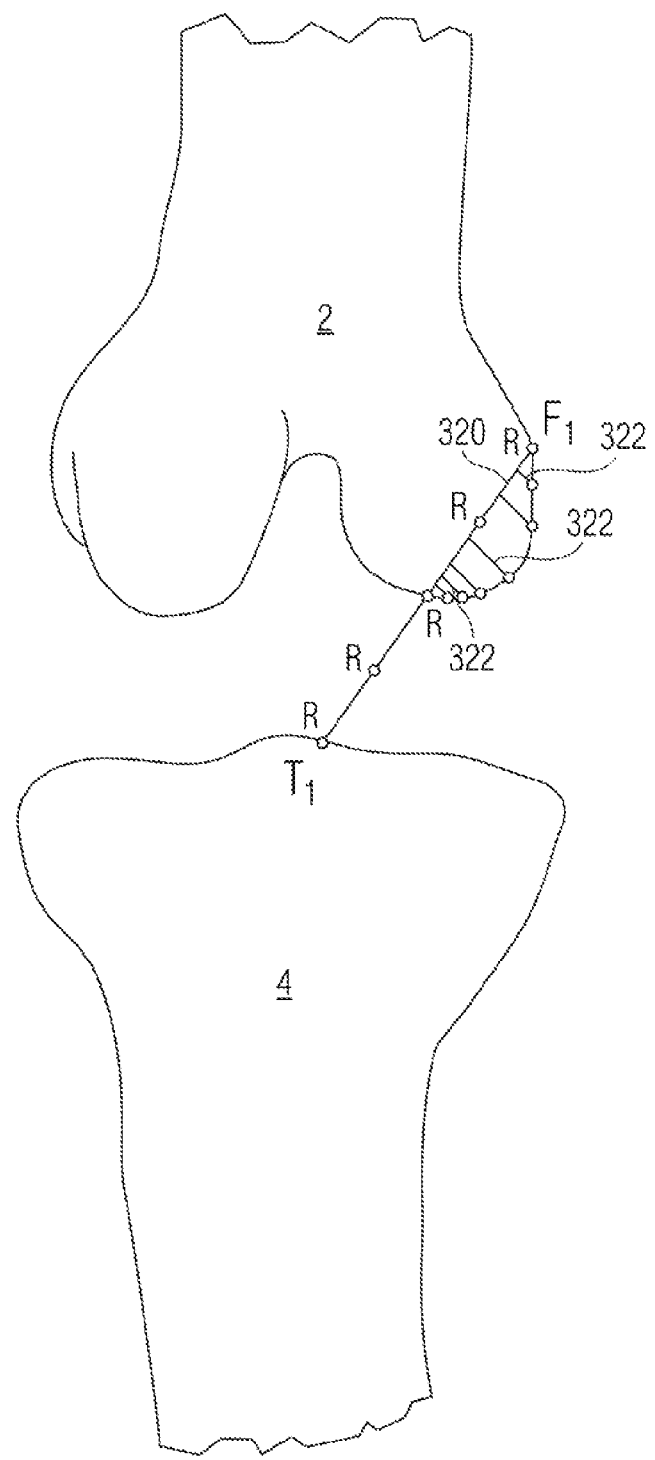
Figure 30:
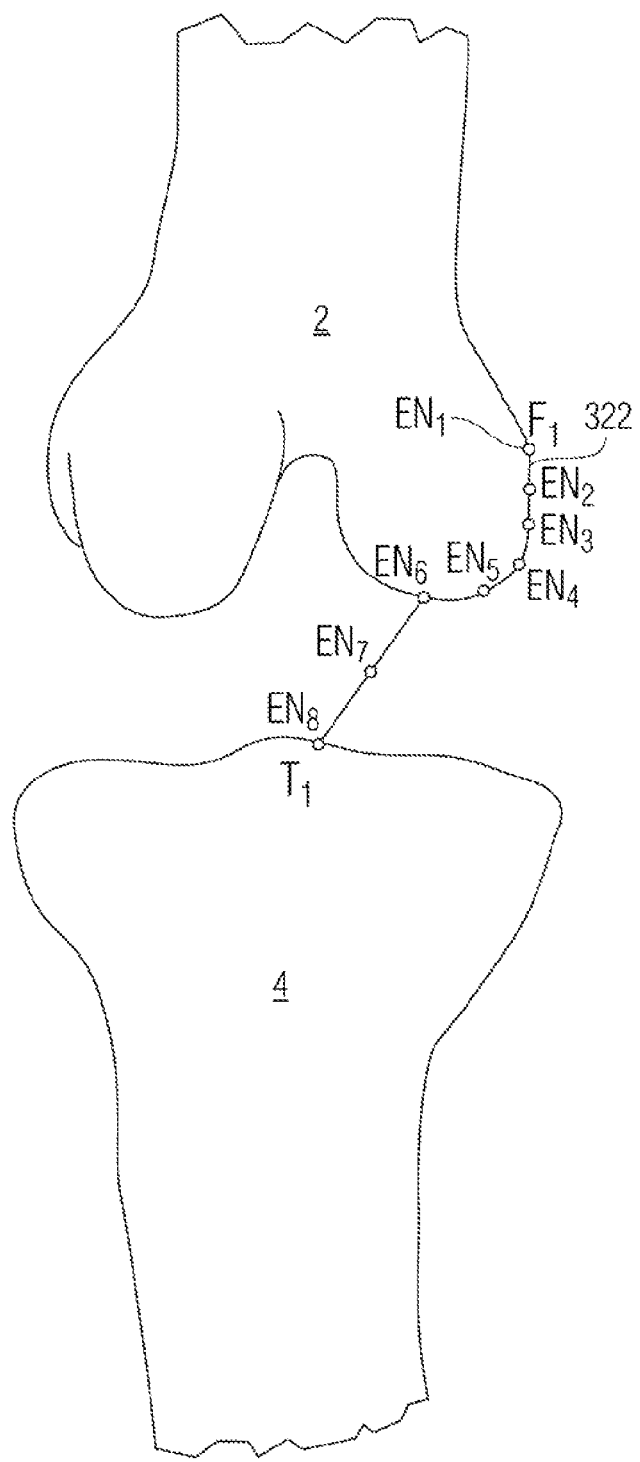
Figure 31:
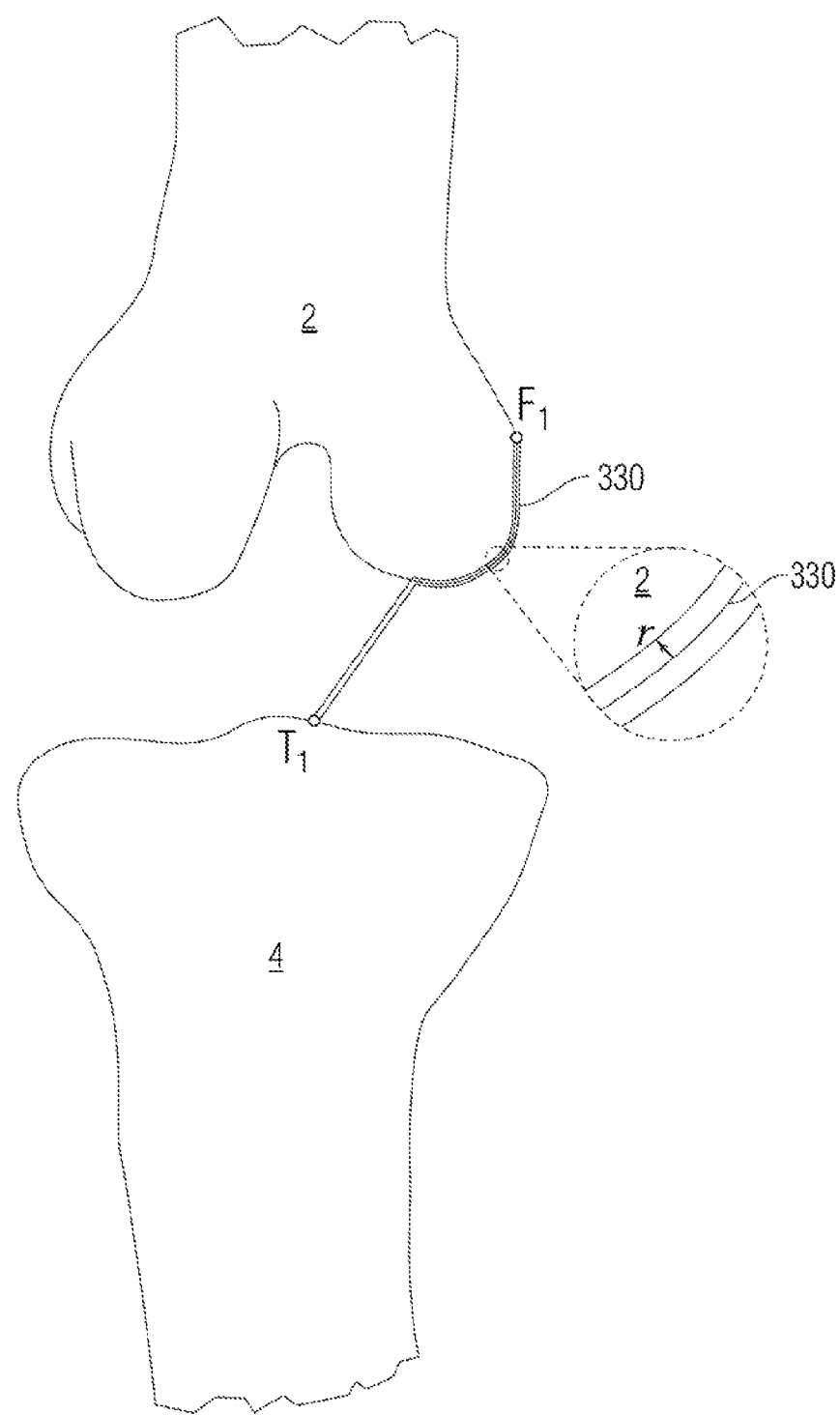

FIG. 5 is a schematic view showing the digitization of a plurality of reference points that are taken for the tibia of the patient and for use in generating a morphological model of the investigated bone portion FIG. 6 is schematic view showing the digitization of a plurality of reference points that are taken for the femoral arch of the patient and for use in generating a morphological model of the investigated bone portion;

FIG. 7 is a schematic showing additional digitization of reference points that are taken for the tibia;

FIG. 8 is a schematic view showing the digitization of a plurality of reference points that are taken for the femur and for use in generating a morphological model of the investigated bone;

FIG. 9 is a schematic view of a graphic representation of results obtained from an anterior drawer test which is part of a number of preoperative laxities tests that are performed to test for joint laxitity;

FIG. 10 is a schematic view of a graphic representation of results obtained from a medio-lateral stability test which is part of a number of preoperative laxities tests that are performed to test for joint laxitity;

FIG. 11 is a schematic view of a graphic representation of results obtained from a Lachman test which is part of a number of preoperative laxities tests that are performed to test for joint laxitity;

FIG. 12 is a schematic view of a graphic representation of results obtained from a pivot shift test which is part of a number of preoperative laxities tests that are performed to test for joint laxitity;

FIG. 13 is a schematic view of a graphic representation of the results of the joint laxities test displayed on the single screen;

FIG. 14 is a schematic view of a graphic representation of a selection of a tibial point and a femoral point as part of an anisometry investigation;

FIG. 15 is a schematic view of a graphic representation of a selection of fixation points by navigating drill guides by aiming the planned fixation points to select the points for analysis of the anisometric data;

FIG. 16 is a schematic view of a graphic representation of a tibial insertion point being digitized by the use of a pointer to select an insertion point of a tunnel;

FIG. 17 is a schematic view of a graphic representation of a femoral insertion point being digitized by the use of a pointer to select an insertion point of the tunnel;

FIG. 18 is a schematic view of a graphic representation of an impingement study to estimate any impingement/contact between the ligament (fiber) and a roof of a notch of the femur;

FIG. 19 is a schematic view of a graphic representation of the digitization of the femoral surface of insertion of the medial collateral ligament using a pointer or the like;

FIG. 20 is a schematic view of a graphic representation of the digitization of an entrance or insertion point of the tibial tunnel using the pointer;

FIG. 21 is a schematic view of a graphic representation to check the anisometry of the medial collateral ligament by evaluating a graph/plot and an anisometry value;

FIG. 22 is a schematic view of a graphic representation of the digitization of the femoral surface of insertion of the external lateral ligament to permit accurate bone morphing;

FIG. 23 is a schematic view of a graphic representation of the digitization of the Gerdy's tubercle with the pointer to define a tibial insertion point for the lateral collateral ligament in LCL reconstruction;

FIG. 24 is a schematic view of a graphic representation of the digitization of the femur insertion point of the LCL with the pointer;

FIG. 25 is a schematic view of a graphic representation of navigation of drill guides by aiming the planned points;

FIG. 26 is a schematic view of a graphic representation of the anisometry of the LCL which is displayed to the physician in terms of anisometry data and value, with the simulated bone morphs and tunnel locations being displayed;

FIG. 27 is a schematic view of the results (values) obtained during the laxitity tests for viewing by the physician;

FIG. 28 is a schematic view of selected fixation points on the tibia and femur used in a method according to the present invention for computing, in real time, the ligament course;

FIG. 29 is a schematic view of a virtual ligament that is calculated and displayed to determine if there is impingement between the virtual ligament and any bone surface;

FIG. 30 is a schematic view of a shifted ligament computed to avoid any impingement that existed between the virtual ligament and the bone surfaces; and FIG. 31 is a schematic view of a computed ligament path that represents the best fit and avoids impingement between the ligament and any bone surface.

DETAILED DESCRIPTION OF PREFERRED EMBODIMENTS

Figure 1:
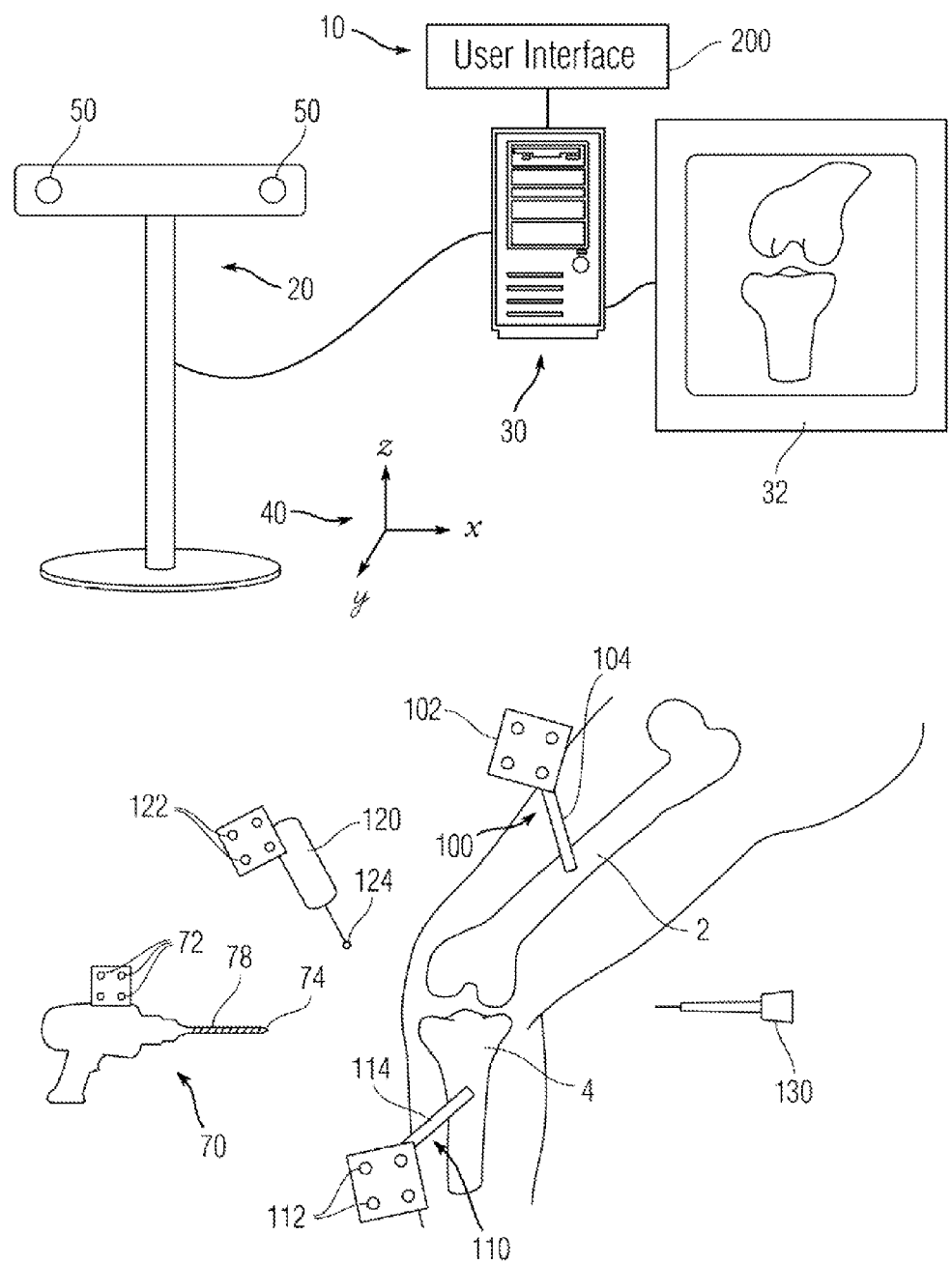
FIG. 1 is a schematic of a computer-assisted orthopedic surgery (CADS) system according to one embodiment.

Referring now to FIG. 1, a computer-assisted orthopedic surgery (CAOS) system 10 is schematically shown. The CAOS system 10 is configured for performing ligament reconstruction surgeries, such as knee ligament reconstruction surgery. The system includes a suitable position measuring device 20 that can accurately measure the position of marking elements in three dimensional space. The position measuring device 20 can employ any type of position measuring method as may be known in the art, for example, emitter/detector or reflector systems including optic, acoustic or other wave forms, shape based recognition tracking algorithms, or video-based, mechanical, electromagnetic and radio frequency systems. In a preferred embodiment, schematically shown in FIG. 1, the position measuring system 20 is an optical tracking system that includes at least one camera that is in communication with a computer system 30 and positioned to detect light reflected from a number of special light reflecting markers, or discs 50.

Detecting and determining the position and orientation of an object is referred to herein as "tracking" the object. To provide precision tracking of objects, markers 50 can be rigidly connected together to form reference bodies, (e.g., 100, 110), and these reference bodies can be attached to bones, tools and other objects to be tracked. One such device that has been found to be suitable for performing the tracking function is the Polaris system from Northern Digital Inc., Ontario, Canada.

The position measurement device 20 is described in greater detail in a number of publication, including U.S. Pat. Nos. 5,564,437 and 6,725,082, both of which were previously incorporated by reference.

The position of the patient's bones, such as the patient's femur 2 and the patient's tibia 4, can be determined and tracked by attaching reference bodies 100, 110, which include respective markers 102, 112. Reference bodies can be attached to bones or tools using pins or screws (104, 114), or various quick release mechanisms. The reference bodies can also be shaped in the form numbers (e.g., "1", "2", "3" . . . ) or alphabetical letters, such as "F" for Femur, "T" for Tibia, "P" for pointer, and so on, so as to avoid confusion as to which reference body should be attached to which bone or tool.

The tracked objects and there relative positions can be displayed on a screen that is connected to the computer system 30. In a preferred embodiment, the display is a touch screen which can also be used for data entry.

The position measurement device 20 includes a number of different tools that are used at different locations and perform different functions as the system 10 is operated to yield optimal ligament graft reconstruction data and information. These tools include the above described markers 50, which act as landmark markers, as well as other tools, such as a drilling device 70 having at least three markers 72 is an example of an object trackable by position measuring device 20. The system also includes a pointer 120, with markers 122, which can be used to digitize points on the surfaces of the femur 2 and tibia 4.

The drilling device 70 also has a drill tip 74 having a known spatial relationship relative to markers 72. Position measuring device 20 determines the position and orientation of markers 72 in the three dimensional coordinate system 40. Based upon the known spatial relationship between drill tip 74 and markers 72, the position of drill tip 74 is determined.

Computer 30 is preferably configured to allow at least one of medical image data and ultrasound data to be used in planning the position and orientation (path) of a hole to be drilled in a bone. The path of a hole being bored by the drill 70 can be monitored and displayed by the computer 30. Thus, the actual path can be compared to the previously planned drill path to allow the practitioner to minimize deviations between the actual procedure and the preoperative plan. In one embodiment the drill 70 is guided to allow the computer 30 to control the drilling path.

The ligament reconstruction system 10 also includes a plurality of reference bodies 100, 110, for determining the position and orientation of an individual's bone in the three dimensional coordinate system 40. The reference bodies 100, 110 are preferably rigid and include respective markers 102, 112, which are preferably configured to emit energy. Each reference body 100, 110 preferably includes a respective attachment element, such as pins or screws 104, 114, with which the reference bodies can be releasably attached to a bone. For example, the reference body 100 is shown as being attached to femur 2. The position and orientation of femur 2 can be determined based upon the position and orientation of markers 102 attached thereto. Markers 102, 112 are sufficient to establish the position and orientation of the rigid bodies 100, 110 within the coordinate system 40.

The system 20 also includes a pointer 120 and endoscope 130, which cooperate to allow a practitioner to digitize landmarks of the femur 2 and tibia 4. Digitizing a landmark comprises determining the position of the landmark in the three dimensional coordinate system, as discussed below. The pointer 120 includes markers 122, which allow the position and orientation of the pointer 120 to be determined in the three dimensional coordinate system 40. The pointer 120 preferably includes a pointer tip 124 having a known spatial relationship to the markers 122. Based upon the known spatial relationship, the position of the pointer tip 124 can be determined from the position and orientation of the markers 122.

In a preferred embodiment of the invention landmark points and or directions are digitised with respect to the femur 2 and tibia 4 with the pointer and are stored in the computer. Preferably an anatomical coordinate system for the femur and the tibia is defined based on at least a portion of the acquired data. The coordinate system could also be defined at least partially using kinematic methods, such as fitting a plane to a trajectory (e.g. fitting the sagittal plane to the flexion/extension trajectory). Possible landmark points include but are not limited to the tibial plateau glenoids, spine, malleoli, the femoral notch, condyles, hip center, bone surface areas, etc.

The ligament reconstruction system 10 of the present invention is preferably an integrated system in which each of the tools is in communication with a master controller, such as the computer 30, which serves to collect all of the data from the individual tools and then process the data to calculate various measurements that are displayable to the physician. The ligament reconstruction system 10 accordingly includes a user interface 200 that is supported by software in the computer 30. The user interface 200 is configured to assist and walk the physician through the ligament reconstruction procedure to obtain optimal results and to assist the physician in determining what the best course of action is in terms of providing and optimizing the stability of the knee.

Figure 2:
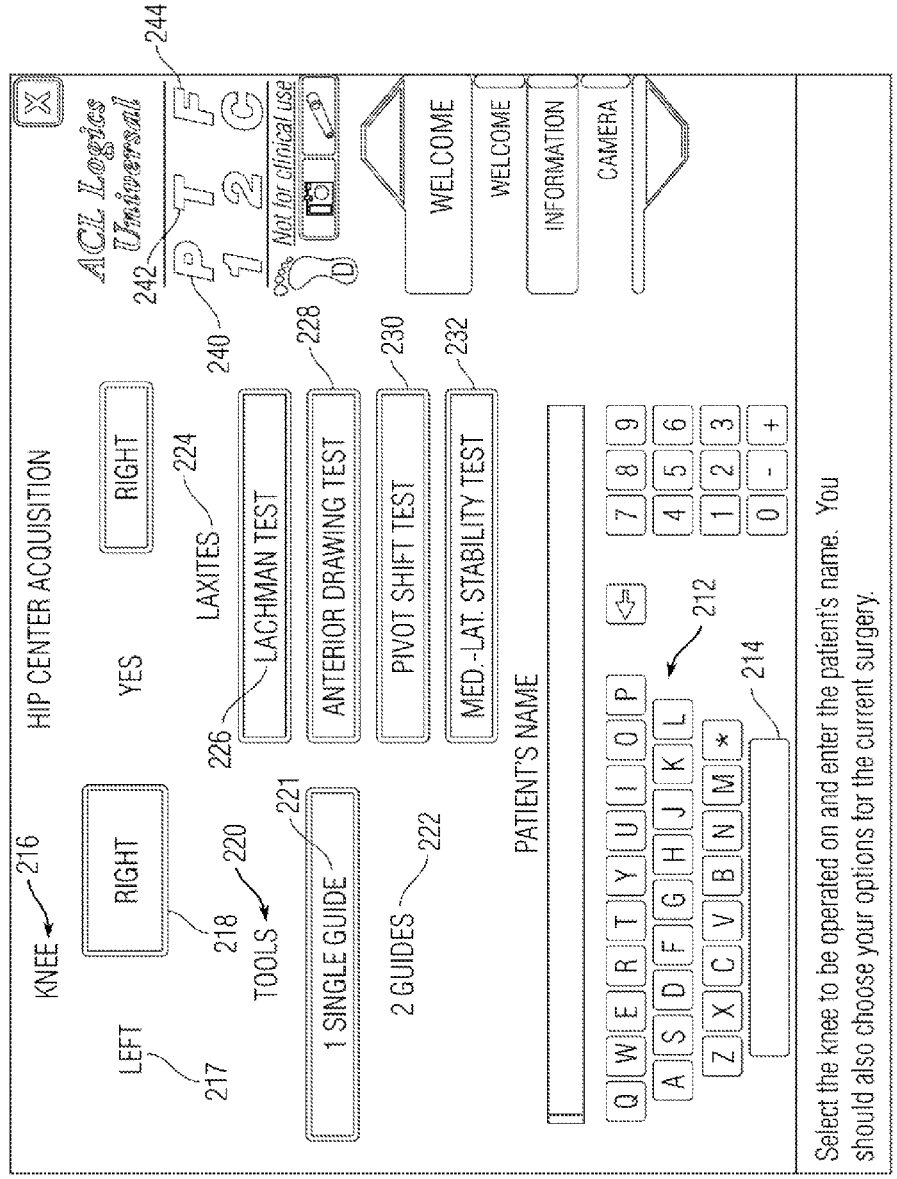
FIG. 2 is a schematic view of a main user interface screen for inputting information related to the surgery.

FIG. 2 illustrates a main user interface page or screen 210 that is preferably displayed on a display 32 (FIG. 1) of the computer 30. The main user interface screen 210 includes a section 212 where the patient's name or other identifying information can be entered using a keypad or the like 214. The main screen 210 also includes a knee indicator box or region 216 which the physician or operator can highlight whether the procedure is being performed on either the left knee (box 217) or the right knee (box 218). The main screen 210 includes a region 220 where tool related information can be entered, as by highlighting a single guide box 221 or a "2 guide" box 222, etc. The main screen 210 further includes a section or region 224 where different operations to be performed during the procedure can be selected by the physician. For example, the region 224 can list a number of different tests that are performed to test the condition and strength of the knee, especially the ligaments thereof, to assist in diagnosing a knee condition, such as a torn ligament (e.g., ACL) or decreased stability in the knee.

In one embodiment, the region 224 lists a number of tests that are associated with the laxity of the joint, in this case the knee. Laxity of a knee is generally the degree of looseness or literally the laxness of the knee and can be determined and tested by moving the tibia 4 relative to the femur 2 and measuring the relative movement of the tibia 4 relative to the femur 2. In the illustrated embodiment, the region 224 includes 4 boxes or sub-regions that can be highlighted and chosen by the physician to test and evaluate knee laxity. The region 224 includes a first box 226 that represents the first test (the Lachman Test); a second box 228 that represents the second test (Anterior Drawer Test); a third box 230 that represents the third test (Pivot shift Test); and a fourth box 232 that represents the fourth test (Medial-Lateral Stability Test).

Other helpful indicia are indicated and provided on the main screen 210 to assist the physician during the operative procedure. For example, the main screen 210 can include icons that indicate whether certain tools are operative and in communication with the computer 30. More specifically, these icons can include a first icon 240 that includes a highlightable letter "P" that represents the pointer 120; a second icon 242 that includes a highlightable letter "T" that represent the second reference body 110 that is for attachment to the tibia 4; and a third icon 244 that includes a highlightable letter "F" that represents the first reference body 100 that is for attachment to the femur 2. As described below, the software and operating system is configured so that when any one of the tools (pointer 120 and reference bodies 100, 110) are in the field of view (vision) for the detection system (e.g., camera), which is necessary for the proper transmission of reference data to the computer 30, the respective icon 240, 242, 244 is highlighted. This makes it easy for the physician to glance at the main screen 210 and see whether all of the tools are in the proper line of sight with the positioning measuring device 20, thereby permitting the free transmission of data (location data) from the tools to the computer 30.

Figure 3:
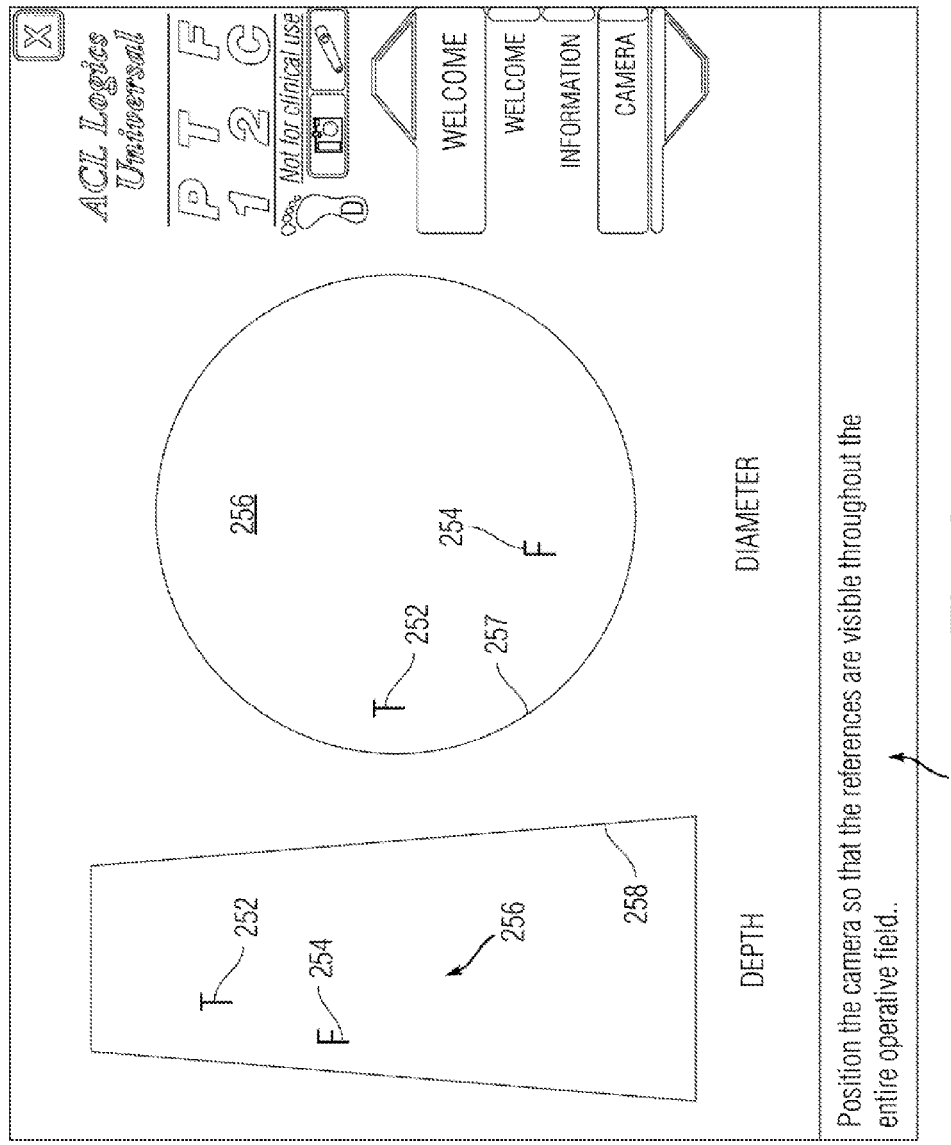
FIG. 3 is a schematic view of a vision screen to assist the physician in positioning of a camera such that the desired tools are within an entire operative field.

More specifically and as shown in FIG. 3, a vision screen 250 is illustrated and is used to assist the physician in positioning of a camera, that is associated with the position measurement device 20, such that the desired tools are within the entire operative field. In the illustrated embodiment, the first and second reference bodies 100, 110 are within the field of vision as evidenced by the P icon 252 and the F icon 254 that are visible in the delineated field of vision 256 which represents the entire operative field. The icons 242, 244 are likewise highlighted (as being illuminated in a different color) to indicate that the reference bodies 110, 100 are visible within the operative field as it is presently set. It will be appreciated that the operative field and the field of vision 256 depends upon a number of parameters, including the precise location of the patient on the operating bed as well as the location of the camera. If either of these parameters changes, then the field of vision 256 will likewise change and one or more of the tools may not be visible to the position measurement device 20. For example, if the patient unexpectedly moved on the operating bed, the patient's leg could move such that the reference bodies 100, 110, attached to the femur 2 and the tibia 4 could fall outside of the field of vision 256. If this occurs, one or more of the icons 252, 254 would move outside of the field of vision 256 on the screen 250 and the physician would then take the appropriate remedial action, such as moving the patient's leg until both icons 252, 254 lie again within the field of vision 256. The illustrated field of vision 256 includes both a diameter display 257 as well as a depth display 258 (which is a two dimensional representation of the field of vision) and it is important that the tools lie within both the field of vision in both displays 257, 258.

Before the pointer 120 is used to determine any position taken by its tip 124, the positioning measuring device 20 is preferably calibrated using any number of different techniques. For example, the pointer 120 is calibrated by placing the pointer tip 124 in a cone of a calibration block. It is important that the pointer should not move during the calibration process. The icon 240 (FIG. 2) is highlighted indicated the pointer 120 is in the field of vision. During the calibration of the pointer 120, the pointer 120 can be slightly tilted a predetermined angle (e.g., 30 degrees) while keeping the tip 124 within the calibration cone. The pointer 120 fitted with markers 122 interacts with the detection system so as to precisely determine any position taken by its tip 124, thereby ensuring calibration. Similarly, a drill guide 78 of the drill 70 is calibrated by selecting precisely the external diameter of the tube of the drill guide 78 and then the guide 78 is calibrated keeping its axis in the groove of a calibration block. The drill guide 78 is turned or rotated by a predetermined number of degrees (e.g., 30 degrees) around its axis, keeping it in the groove in order to ensure the accuracy of the calibration. The extremity of the drill guide 78 is placed on the calibration plane perpendicular to the surface. The physician then operates an actuator, such as a foot pedal, to initiate calibration of the drill guide 78.

To perform computer assisted orthopedic surgery, especially ligament graft reconstruction, using the present system 10, the reference body 100 is attached to the femur 2 at a selected point, as by screwing the reference body 100 into the bone with screw 104. The reference body 100 includes the first set or triplet of photoemitters 102 that are thus fixed to the femur 2 at the point. Similarly, the reference body 110 is attached to the tibia 4 at a selected point by screwing the body 110 into the bone with screw 114. The reference body 110 includes the second set or triplet of photoemitters 112 that are likewise fixed to the tibia 4. Since the reference bodies 100, 110 are fixed to the bones 2, 4, the pointer tip 124 can be used to point at any given point on bone 2, 4, the position of which is precisely taken by its tip 124. Then, it is possible using a conventional data processing system to determine the vector connecting the point where the respective body 100, 110 attaches to the bone 2, 4 to the point of the tip 124, and therefore, locate any given point for any position of the femur 2 or tibia 4.

Figure 4:
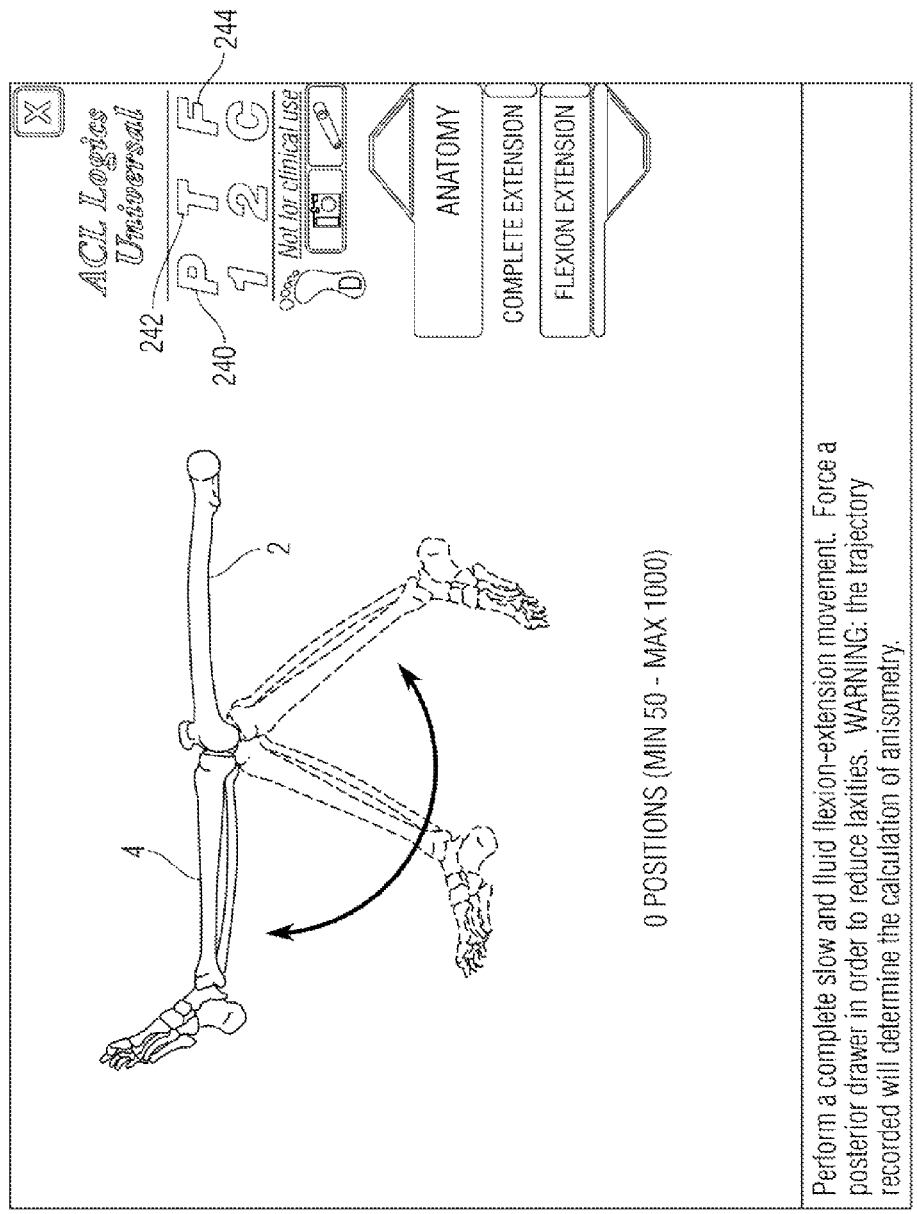
FIG. 4 is a schematic view of a screen showing a complete slow and fluid flexion-extension movement to assist the physician in determining the anatomy of the patient.

According to one exemplary method, a number of different reference points are obtained using a digitization technique that is part of a bone morphing system. For example, the pointer tip 124 is used to digitize the external malleolus by placing the pointer tip 124 at this bone location which is determined and stored by position measurement system 20. As can be seen, the icons 240, 242 are highlighted indicating they are in the field of vision. Next the internal malleolus is digitized by placing the pointer tip 124 at this location. The leg is placed in complete extension and neutral rotation as shown in FIG. 4 and this position is used to project the femur 2 onto the tibia 4 during navigation (icons 242, 244 highlighted). A complete slow and fluid flexion-extension movement is performed as shown in FIG. 4. A posterior drawer is forced in order to reduce laxities. Since the reference bodies 100, 110 (not shown) remain fixed to the femur 2 and the tibia 4, the relative movements can be recorded.

According to the present invention, additional reference points are gathered. More specifically, another reference point that is determined and mapped is the summit of the external spline 266 of the tibia 4 which is digitized using pointer 124 as shown in FIG. 5. Once again, this location is easily determined using a conventional data processing system since a vector can be generated between the summit point and the anchor point of the reference body 110 and therefore, the external spline summit point can be determined. Similarly, the internal spline summit 267 is digitized using pointer 120 as shown in FIG. 5.

Additional reference points are taken for the tibia 4 by placing the pointer 120 on an external glenoid 268 as shown in FIG. 5 to thereby digitize the external glenoid 268 (icons 240, 242). An internal glenoid 269 is digitized using the pointer tip 124 as well as a middle of an interior inter-meniscal ligament 270 of the tibia 4. The glenoids 268, 269 represent tibia plateau surfaces. Thus, the precise locations of the two glenoids 268, 269 and the middle of the anterior inter-meniscal ligament 270 are calculated using the position measurement system 20 and as will be described hereinafter, these locations or points on the identified morphology of the patient's bones are used in the present system to calculate the joint (knee) laxity to assist in an improved restorative knee operation. During this digitization process, the operator merely runs the pointer tip 124 along the bone and then when it is desired to collect a reference point, the operator simply manipulates the system as by pressing a button or the like to signal the system to collect data for the selected reference point.

Acquisition or data points are also taken for the femur bone 2 and more particularly, the pointer 120 is moved along the surface of a femoral notch 5 of the femur bone 2 in order to digitize the middle of the arch of the femoral notch 5 at approximately, the "12 o'clock position", in practice in the prolongation of the lateral border of the posterior cruciate as shown in FIG. 6. Next additional selected surfaces of the tibia 4 and the femur 2 are investigated and data points are taken and more particularly, the peri and inter-spinal surface of the tibia 4 is digitized using the pointer 120 as shown in FIG. 7. In all of these steps, the digitization occurs by locating and logging a selected bone surface point in the three dimensional coordinate system 40 and by using the data processing system. In other words, the pointer 124 is moved along the bone surface and coordinate data are gathered for use in generating a morphological model of that bone portion.

Yet another feature of the present invention is shown in FIG. 7 in which a bar meter 280 or the like is shown for indicating the amount of data points that have been captured and digitized and stored as acquisition points. In other words, the bar meter 280 is initially empty indicating that no data points have been captured and as the physician moves the pointer 120 around the femur bone surface (peri and inter-spinal surface), a bar 282 begins to grow within the meter 280. As more acquisition points are captured, the length of the bar 282 grows and the user is generally made aware of the amount of acquisition points that left before the system 10 deems the data acquisition step complete and moves on to the next step or operation (e.g., next data acquisition). Accordingly, once the bar 282 extends completely to the right of the meter 280 and fills up the entire meter box 280, then the specific data acquisition step is deemed to be complete since a sufficient number of data points have been acquired. The meter 280 helps assist, in real time, the progress of the data acquisition and for example, if the user has concentrated too heavily on collecting data points in one particular local area, while ignoring other important areas, then the ever increasing length of the bar 282 in the meter 280 can serve as a reminder that it is time to move on to the other areas to collect data.

As previously mentioned, the pointer 120 can be actuated to begin data acquisition by simply activating an actuator, such as a foot pedal in which case it is merely depressed by the physician. The above described digitizing process can be thought of as a landmark acquisition process. Thus, according to a preferred embodiment of the present invention, landmark points and/or directions are digitized with respect to the femur 2 and the tibia 4 utilizing the pointer 120 and are stored in the computer 30. Preferably, an anatomical coordinate system for the femur 2 and the tibia 4 is defined based on at least a portion of the acquired data. The coordinate system can also be defined at least partially using kinematic methods, such as fitting a plane to a trajectory (e.g., fitting the sagittal plane to the flexion/extension trajectory). As discussed in some detail above, possible landmark points include but are not limited to the tibial plateau glenoids, spine, malleoli, the femoral notch, condyles, hip center, bone surface areas, etc. The data acquisition points can be used to determine other information, such as locating a mechanical axis of the tibia 4.

In a preferred embodiment of the present invention, three dimensional geometrical surface models of the bones are provided by image-free means. Preferably these models are obtained by adjusting a deformable model of the bone to points acquired on the bone surface. Examples of some known methods of carrying out this task can be found in the following references: (1) "Building a complete surface model from sparse data using statistical shape models: application to computer assisted knee surgery" by M. Fleute and S. Lavallée, published in Medical Image Computing And Computer-Assisted Intervention—MICCAI'98, Spinger-Verlag LNCS Series, pages 880-887, October 1998; (2) Fleute M, Lavallee S, Julliard R. Incorporating a statistically based shape model into a system for computer-assisted anterior cruciate ligament surgery. Medical Image Analysis. 1999 September; 3(3):209-22. However, other known methods of obtaining geometrical bone models in surgery exist (for example, matching medical image data such as CT, MRI, etc, to points acquired with a pointer or an ultrasound probe). Each of the above listed references is hereby incorporated by reference in its entirety.

In particular, the three dimensional shapes of the involved bones may be provided with image free techniques, such as using bone morphing software which is capable of extrapolating very few range data to obtain a complete surface representation of an anatomical structure (e.g., a bone). The specific details of bone morphing are set forth in the above references but in general, a complete surface model is built from sparse data using statistical shape models. In particular, the model is built from a population of a number of specimen (points), such as femur or tibia points, that are digitized. Data sets are registered together using an elastic registration method (e.g., the Szeliski and Lavallee method) based on octree-splines. Principal component analysis (PCA) is performed on a field of surface deformation vectors. Fitting this statistical model to a few points in performed by non-linear optimization. Results can thus be presented for both simulated and real data. This method is very flexible and can be applied to any structures for which the shape is stable.

In a preferred embodiment of the invention representations of the femur and tibial bones, or a portion thereof, are displayed on the screen. These models move on the screen in real time based on the motion of tracked femur and tibia. In a preferred embodiment of the invention the system guides the surgeon in manipulating the knee, by using the bone representations as visual aids. Knee manipulations are preferably preformed for both "normal" and "abnormal" joint motions. Normal motions can include passive flexion/extensions of the knee, with the tibia guided by the medial and lateral femoral condyles. Abnormal joint motions are those indicative of instability in the joint, such as those described in above-mentioned chapter by Scuderi.

In other words, the present system preferably is configured to collect data with the pointer 120 in order to perform bone morphing operations or procedures to thus obtain three-dimensional geometrical surface models of the bones. During typical bone morphing, the representation of the bone (in this case the tibia 4) on the display 32 of the computer 30 includes shading or some other type of indicator that highlights the areas of the bone that have increased accuracy due to the physician having collected a number of data acquisition points in this region. For example, the areas where more data points were collected are shaded differently or displayed in a different color and the accuracy of the bone morphing (i.e., tibial bone morphing) on the cartilaginous and bony surface can be checked. Areas of the bone that have not been scanned using the pointer 120 are simulated using conventional extrapolation techniques as commonly found in bone morphing techniques and systems.

Similarly, target locations of the femur 2 are digitized and as illustrated in FIG. 8, and in particular, a roof and the lateral notch of the femur 2 are preferably digitized as well as the anterior arch in the area of potential conflict as shown in FIG. 8 (note: icons 240, 242 are highlighted and bar 282 in the meter 280 indicates the number of data acquisition points collected). On the display screen, the system preferably indicates where the pointer 120 has traveled and collected data acquisition points as by providing a visual colored point representation on the screen. As with the tibia 4, bone morphing for the femur 2 is performed and a representative bone morph is displayed to the physician. Shading or some other type of indicator is used to highlight the areas of the bone that have increased accuracy due to the physician having collected a number of data acquisition points in this region (in this case around the arch and notch).

In order to assess the patient's condition and to better assist the physician in diagnosing the patient's condition and recommending a remedial action, the present system 10 preferably guides the physician through a number of different motion protocols that are part of tests to be performed to assess the patient's condition. For example, a number of preoperative laxities tests can be formed to test for joint laxity. One such test, shown in FIG. 9, is an anterior drawer test and involves manipulating the bones (femur 2 and tibia 4) through a range of movements and collecting data as a result of the reference bodies 100, 110 being attached thereto. More precisely, the test is performed with the patient lying on their back with their knee in 90 degrees of flexion, with the foot resting firmly on the table. The physician grasps the top portion of the skin with both hands, positioning the thumbs on either tibial condyle 13, 15. Stabilizing the foot, the physician places pressure slowly on the proximal tibia by moving the shin toward the physician. Abnormal looseness and movement forward indicated a significant ACL injury. In other words, the motion and track of the reference bodies can easily be observed and stored in memory and from this data, the looseness and movement can be quantified and displayed to the physician in real time on the display screen.

In one aspect of the present invention, an on-screen guide 17 is provided to summarize measured test values for the data acquisition points for the drawer test and offer a unique visual tool to the physician to show in real time how the current position between the femur 2 and tibia 4 corresponds to other positions between the two bones. More specifically, FIG. 9 shows a user interface tool 17 which displays the movement of the tibia 4 relative to the femur 2 during the laxity test, in this case the drawer test. In particular, the tool 17 has a first indicator 19 to represent the results of the medial stability measurement, a second indicator 21 to represent the results of the lateral stability measurement, and a third indicator 23 to represent the results of the axial rotation measurement. Each of the indicators 19, 21, 23 graphically illustrates a range of the data for the respective measurement (medial and lateral stability and axial rotation) taken for the captured reference points and each includes a locator 25 that highlights the measurement value for the current position of the tibia 4 relative to the femur 2.

In the illustrated embodiment, the locator 25 is in the form of a ring, of different color, that surrounds the respective indicator which is in the form of a column. The locator 25 also shows the exact measurement value next to the column. The relative position of the locator 25 axially along the column represents how the current measurement value compares to the other measurement values. For example, FIG. 9 show that the current position between the tibia 4 and femur 2 results in a medial stability value of 3 mm (anterior) (as indicated by the highlighted "3" next to the bar column) which lies closer to the maximum measured value of 5 mm (anterior) and far away from the posterior measured value of 4 mm. The range of the bar column is 9 mm (anterior 5 mm+posterior 4 mm). The other indicators displays (columns) 21, 23 have similar locators 25 so that the operator, in real time, can simply look at the screen display and see how the acquired values for the current bone position compares to other bone positions. In another aspect, the neutral position along the indicator (column) can be indicated as a line or interface between two different colored column portions. For example, the column (indicator) has two different colors along its axial length, with the neutral position being indicated where the two different colored portions abut. This demarcation permits the operator to easily ascertain the neutral position and see in real time how far away or close the current position is from the neutral position and how movement of the tibia 4 changes this relative position.

It will be understood that the guide tool 17 (indicators) can be used to show the measurements of the other laxity tests and indicate the neutral positions of the test measurements.

A second pre-operative test is a medio-lateral stability test shown in FIG. 10, while a third test is a Lachman test shown in FIG. 11. In the Lachman test, the femur 2 is grasped with one hand, while the tibia 4 is pulled forward and the amount of excursion noted. In normal subjects, no forward movement is elicited.

A fourth test that tests for laxity is the pivot shift test which is shown in FIG. 12. The location of the anterior inter-meniscal ligament (represented by previously acquired points) is used during the pivot shift test and more specifically, it is this point that is the preferred reference point of the tibia 4. The pivot shift test is a test for anterior cruciate stability. When this ligament is lax, the pivot between the lateral femoral condyle 13 and the tibial condyle 15 is unstable. Thus, if the knee is medially rotated, the tibia can be displaced forwards with respect to the femur 2. This subluxation is spontaneously reduced when the knee is flexed, giving a palpable or visible jerk. One of the disadvantages of conventional pivot shift testing was that there was no associated value or quantification of the results; but rather, the physician would simply manipulate the leg and then use his past experience to assess the patient's current condition.

To generate a value representing the result of the pivot shift test, two plots can be plotted and compared to one another, namely a first plot (reference or neutral plot) that represents the laxity as a function of degree of flexion of the patient's leg prior to performing the pivot shift and a second plot which plots the motion of the leg after the pivot shift (dislocation) has been performed. As would be expected, the laxity value over the degree of flexion is greater for the plot after the pivot shift is performed on the knee and therefore, there is a distance between the two plots. Thus, for any given angle of flexion, two values can be compared, one value for the neutral knee position and another value for the knee with the pivot shift, thereby permitting the difference between these two values to be quantified.

Preferably, the system and software is configured to look for and determine the maximum distance or maximum translation between the neutral and pivot shift positions for each given angle of flexion and this value shown in FIG. 13 is displayed as Delta Max and is quantified in units, such as millimeters, and is displayed in real time on the screen. In other words, the values of the two plots for the same degree of flexion are compared and then the largest difference is taken as the Delta Max value and is displayed.

Note that for all these tests, the icons 242, 244 are highlighted indicating that the reference bodies 100, 110 are in the field of vision 256.

One advantage of the present system is that the results on the tests are quantified and displayed in real time to the physician. Since the position measurement system 20 monitors in real time the positions of the two bones due to the reference bodies 100, 110 being attached thereto, one or more values can be generated that quantify the test results. As shown in FIG. 13, the results of the four tests can be displayed on a single screen. The results have associated values that are displayed to assist the physician in evaluating the particular patient's condition and assist in selecting appropriate remedial action, such as reconstructive surgery. For example, the physician can review the results and more specifically, the quantitative values generated and displayed for each test and then decide what type of surgical procedure should be undertaken. More particularly, there is a strong link between the laxity values and a determination of whether extra articular stabilization is needed for the patient. Extra articular stabilization is a technique by which not only is the anterior ligament (ACL) replaced but also the ligament is routed to the exterior portion of the knee to provide extra articular stabilization by being fixed between the tibia 4 and the femur 2.

By easily calculating and displaying in real time, the results of the laxities tests, the present invention provides the physician with a tool that is used to determine not only how to optimize the placement of the ACL but also whether additional surgical procedures may be needed, such as extra articular stabilization or medial or lateral ligament reconstruction. The system 10 is preferably a stand-alone unit that is provided at the operative site and gives the physician a helpful, real time visual guide.

After performing the above-described pre-operative tests, the next step is to determine and locate both a tibia point ($T_1$) and a femur point ($F_1$) that produces optimal isometry. As is known in the relevant art, isometry involves a measurement of length change between selected replacement ligament (e.g., cruciate ligament) insertion site with a passive range of motion. When no length change occurs through a normal unrestricted motion arc, the reconstruction is said to be isometric. According to some conventional thought, anisometry of no more than 2 millimeters, through a range of from 0 to 90 degrees, is thought to produce satisfactory cruciate placement precision. It is therefore desirable to maximize isometry, thereby minimizing the length change of the ligament. As will be described below, while conventional computer assisted surgery system minimized isometry based on a linear model between a point on the tibia 4 and a point on the femur 2, the present invention takes into account that in reality, the replacement ligament is unlikely to be able to travel in a straight line (linear) since bone shapes and in particular the topographical features of the bones interfere with the placement and travel of the ligament. Thus, any impingement needs to be taken into account when selecting the points $T_1$ and $F_1$. As set forth below, the present invention is configured to calculate an isometry value that is truer or closer to the realities of the operative site since the topographical features of the bones can be taken into account due to the bone morphing capability of the present invention.

Next, an anisometry investigation is undertaken to determine the anisometry characteristics of a selected tibial point and a femoral point. As shown in FIG. 14, a tibia point is selected as a well as a femoral point using either the pointer 120 or the drill guide 78 of drill 70 (note icons 240, 242, 244 are highlighted). To record each point on the femur 2 and the tibia 4 after the pointer 120 (or drill guide) is positioned on the bone itself as by screwing into the bones and then the physician activates the actuator (e.g., depressing a foot pedal) to record each of these points. As shown in FIG. 14, all three icons 240, 242, 244 are highlighted since all are in the field of vision.

One helpful feature of the present invention is shown in FIG. 14, where the previously recorded (digitized) points are highlighted and the precise relationship between the two bones 2, 4 is shown by projecting the condyles 13, 15 of the femur 2 on to the tibial surface 2. In FIG. 14, the projected condyles 13, 15 are shown as shadows on the tibial surface. The physician can thus see the relationship between the digitized points of the tibial surface and the projected condyles 13, 15. FIG. 15 shows that when investigating and calculating the anisometry of a ligament between the two selected points, it is helpful to plot in a graph 300 (also can be referred to as an anisometry map) the length of the ligament on the y axis and on the x axis, the flexion (in degrees) is plotted. In yet another feature of the present invention, the graph includes indicators, generally indicated at 290, 292 for quickly indicating to the physician if the system is operating normally. In other words, the indicator 290 is in the form of an arrow having an increasing slope, while the indicator 292 is in the form of an arrow having a decreasing slope. The arrow 290 is labelled with the word "INCORRECT" to indicate that if the slope of the plotted points (graph) is in the same direction as the arrow 290 (i.e., positive slope), there is something wrong with the operation since the plotted points should instead have a negative slope of flexion similar to the arrow 292 which is labelled as "CORRECT". The arrow 290 can have a red color to indicate an undesirable event since red is associated with a traffic stop or danger, while the arrow 292 has a green color to indicate proper operation and a desirable event since green is associated with go at a traffic stop, etc.

The drilling device 70 is navigated by aiming the drill tip 74 at the target locations on both the tibia 4 and the femur 2. As shown in FIG. 15, both the tibia 4 and the femur 2 are displayed on a single screen with the condyles 13, 15 being superimposed on the tibia 4 in the window that shows the tibia 4. It will be appreciated that each window shows an image of the tibia 4 and the femur 2 that is generated using bone morphing technology as previously mentioned. Bone morphing advantageously permits the target locations of the tibia 4 and the femur 2 to be shown topographically. For example and as shown, the femoral notch of the femur 2, which was the area of the highest amount of digitized points, includes a topographical layout to assist the physician in selecting a desired location to locate an anchor point in the femur 2. As shown in the graph 300, a plot is generated to illustrate the anisometry characteristics of a ligament placed between the two selected points $T_1$ and $F_1$ and more particular, the graph 300 plots of the length of the ligament over a degree of flexion for a ligament that is attached between the two selected points. A quick glance of the graph 300 will indicate to the physician that the system is operating normally and that the physician has correctly performed all steps since the plotted line has for the most part a negative slope.

As mentioned, the present invention is able to provide the physician in real time with a quantitative anisometry value to permit the physician to easily compare different sets of target anchor points in order to minimize the isometry. In FIG. 39, the anisometry value is indicated in or near the graph 300 and in the illustrated embodiment, this value is 4 mm. Also of interest, is that region 310 of the screen lists the selected diameter of the replacement ligament and buttons 312, 314 can be used to either increase or decrease, respectively, the diameter. The diameter of the replacement ligament is taken into consideration when determining the true anisometry value according to an algorithm that is used in the present system 10. As the diameter of the ligament increases, the change in trajectory of the ligament creates a bigger impact on the anisometry value.

As mentioned above, one of the disadvantages of the conventional computer assisted systems for determining the position of the femur point and tibia point for minimizing the anisometry is that these systems do not account for interference of impingement of the ligament by the bone surfaces; but rather, they merely calculate anisometry on the assumption that the ligament follows a straight line between the two points. In direct contrast and according to a preferred embodiment of the present invention, the locations of the preferred fixation points (anchor points) of the internal and external ligaments on the femur 2 and tibia 4 can be computed using an algorithm that detects and accounts for interference or impingement of the ligament with the surfaces of the bones 2, 4 that have been modeled in a computer-based system according to one embodiment of the invention, thereby overcoming the deficiencies associated with the conventional systems. This is preferably accomplished in a computer simulation that uses a geometrical algorithm to simulate the ligament wrapping around or contact any bone modeled surface that might be along its path between the two selected fixation points.

One possible method of computing the ligament course (path of travel) in real time is to use a numerical simulation that approximates the trajectory of the ligament. The application of the algorithm can be illustrated with reference to FIG. 28 which illustrates a selected fixation point $T_1$ on the tibia 4 and a selected fixation point $F_1$ on the femur 2. Next, the fixation point $T_1$ is connected to the fixation point $F_1$ with a "virtual" (initially straight) ligament, shown by a line 320 between the two points. A check is then made to see if this virtual linear ligament 320 extends through or contact any bone surface 2, 4. In other words, an analysis is performed to see if there is impingement of the virtual ligament 320 with one or more of the bone surfaces 2, 4. If there is impingement, then the virtual ligament 320 is divided into a number of smaller ligament segments with end points R as shown in FIG. 29. Each segment with end point R that extends or lies at least partially inside a bone (i.e., an impinging ligament segment) is projected onto the bone surface in the direction of the shortest vector 322 from the corresponding point to the bone surface. For purpose of illustration only, FIG. 29 illustrates the situation where the virtual ligament 320 passes through the inside of the femur 2 and thus is impinged by the femur 2.

Next, the projected ligament is further subdivided and the above steps are repeated until the virtual ligament 320 no longer substantially interferes with the bone (femur 2). In other words, the ligament is subdivided and the each subdivided ligament segment that still falls within the bone (still impinges) is projected onto the bone surface. After the aforementioned has been accomplished, the line representing the ligament is shifted in a direction normal to the surface by a value equal to the ligament radius r and if a straight line can be drawn between any non-neighboring endpoints within the ligament without crossing the bone, the intermediate endpoints between the neighbors are deleted (i.e., this simulates ligament tensioning). According to one embodiment, one of the non-neighboring endpoints is the endpoint R at the anchor point of one of the bones (in other words, one actual end of the ligament), as shown in FIG. 30 by the legends $EP_1$ (endpoint 1 near the femur surface) and $EN_8$ (endpoint 8 at the anchor point of tibia). The endpoints $EN_2$ through $EN_7$ represent other endpoints of the ligament segments. As shown in FIG. 68, a straight line can be drawn between $EN_4$ and $EN_8$ without crossing the bone and therefore, endpoints $EN_5$-$EN_7$ can be eliminated and the ligament path is a straight line between $EN_4$ and $EN_8$.

Finally, the ligament diameter is taken into account by shifting the centerline of the ligament away from the bone surface by radius r since the ligament is a three-dimensional object. As shown in FIG. 30, the final resulting ligament line 330 is not a straight line, as is the case of the initial straight line 320, but rather the final simulated ligament 330 has a trajectory that accommodates the topographical features of the bones and lies entirely outside of the bones 2, 4 (i.e., does not extend through or impinge any of bones 2, 4).

To minimize the anisometric value and locate the optimal fixation points, the physician moves the pointer 120 over both surfaces of bones 2, 4 in target areas to locate and find the optimal fixation points that not only minimize the anisometry value of the ligament but also minimizes the impingement, if any, of the ligament. Once again, to select the fixation points, the physician merely depresses the actuator (foot pedal) or performs some similar action to indicate to the system that the location where the pointer tip 124 is located is to be recorded and stored and processed as one of the selected fixation points. It will also be appreciated that the algorithm is used to calculate the anisometric value throughout the whole range of extension/flexion, thereby generating a true graph 300 that offers and yields a more complete anisometric value that is used by the physician to select the proper fixation points and to select the appropriate ligament length to be used in the operation. Thus, for any two fixation points ($T_1$ and $F_1$) that are selected a graph or plot 300 is generated to show the true length (as determined by the above algorithm) of the ligament over a range of flexion degrees. FIG. 15 shows different fixation points being selected for analysis of the anisometric data. The present system 10 is thus a real time system that looks and takes into account the anatomy of the patient when assessing and determining the optimal fixation points for the ligament.

In yet another aspect, the present invention is configured to assist the physician in locating and selecting the proper locations for the tunnels that are formed in the tibia 4 and the femur 2 that terminate at the desired fixation points on each bone surface. More specifically, once the fixation points are located on the bone surface, the next consideration is that the location of the tunnels has to be determined since the ends of the ligament are anchored at the fixation points to fixation devices, such as screws, that are disposed within the respective tunnels formed in the bones 2, 4. As shown in FIG. 15, the selected fixation points are indicated in the displays by a "bull's eye" type indicator 400, with the center of the bull's eye indicating the center of the selected fixation point.

A tibial tunnel is thus formed in the tibia 4 with the tunnel having an insertion point at one end and the other end being the end that terminates at the tibia fixation point formed on the tibial surface. It will be appreciate that there are any number of different paths (tunnels) that can be formed that enter the tibia 4 at one location and exit the tibia 4 at the tibial fixation point. In other words, the selection of an insertion point will set or determine the location of the tunnel since it must terminate or exit at the fixation point and therefore, varying the insertion point will alter the entry angle of the tunnel as well as the length of the tunnel. FIG. 16 shows a tibial insertion point being digitized by use of the pointer 120 and more particularly, at this point in time the system is set in a mode to determine the tunnel location and characteristics, the pointer 120 is placed on the tibial surface to select an insertion point for the tunnel. It will be noted that icons 240, 242 are highlighted. Once the two end points are selected, a simulated tunnel is displayed for the physician to observe and useful tunnel information is supplied. The physician can see if the tunnel angle is appropriate and that the tunnel is located and formed in a sufficient density of bone such that formation of the tunnel will not result in fracturing of the tibia 4. In addition, the present invention contains a feature not found in other conventional systems in that the user interface and software is programmed to calculate the depth of the tunnel and provide the physician with this value on the display (screen). Since the pointer 120 and location of the fixation point are points in the three dimensional coordinate system, the distance between the two can easily be calculated using a conventional data processing system. It is helpful to provide the physician with the tunnel depth since this permits the physician to select the appropriate sized anchor or fixation device, such as a screw. Screws come in different standard lengths and therefore, it is desirable for the physician to try to best match the length of the screw with the depth of the tunnel so that the screw does not protrude beyond the tibial surface and thereby perhaps interfere with the femur, etc., and equally, it is desirable for the screw to not be too far away from the tibial surface when placed in the tunnel.

In yet another feature, not only is the exit port of the tunnel displayed (it being desirable for the exit port of the tunnel to match the center of the bull's eye 400) but also the periphery shape of the exit port is displayed on the tibial surface. The fixation point (bull's eye) is depicted as a perfect circle; while the peripheral shape of the exit port of the tunnel will vary on a number of different parameters, including the specific path of the tunnel through the bone. The degree of entry of the tunnel into the bone at insertion point will vary the peripheral shape of the exit port since if the insertion point is relatively shallow and close to the tibial surface with the tunnel extending substantially across the width of the tibia 4, the exit port will be more oval shaped as opposed to a circle (this situation is likely not desirable since a shallow tunnel can lead to bone instability and fracture when drilling the tunnel). Thus, it is typically desirable for the peripheral shape of the exit port of the tunnel to more approximate a circle.

Similarly, the same steps are taken to determine an optimal femoral insertion point as shown in FIG. 17. As with the tibial tunnel, data is provided to the physician that corresponds to the depth of the tunnel and the location of the tunnel as well as the peripheral shape of the exit port. Next as shown in FIG. 18, it is desirable to perform an impingement study to estimate any impingement/contact between the ligament (fiber) and the roof of the notch of the femur 2. Also, the anisometry of the ligament is displayed in graph/plot 300 with the anisometry value being given (in this case 7 mm) as well as a maximum impingement value (in this case 11 mm). As shown in FIG. 16 and as previously mentioned, the condyles 13, 15 are projected on the tibial surface since this will permit the physician will locate the tunnel exits ports and the ligament such that the ligament does not lie in this shadowed area that represents the projected condyles 13, 15 since such a position will result in 100% impingement of the transplant ligament. In addition, after the tibial tunnel is formed, the physician has an opportunity to reselect the femur fixation point to obtain a more optimal isometric graph. It will be understood that common drilling techniques include the formation of a pilot hole first before the entire tunnel is drilled and therefore, the formed pilot hole can be checked against the selected fixation point to see if the exit port of the pilot hole matches the center of the bulls eye and if it is outside of some tolerance value, the physician can take appropriate remedial action, such as reselection of the femur fixation point as mentioned above.

Once the tibial and femoral tunnels are formed, the precise length of the ligament is computed using the above algorithm that takes into account the topographical features of the bones 2, 4. The use of the above algorithm takes into account the true trajectory of the ligament as it passes between the two fixation points and during normal extension/flexion. This results because of the incorporation of bone morphing technology and techniques into the present system resulting in a truer, more accurate anisometry value being generated and displayed quantitatively to the physician.

A final report or final display screen where various information is preferably provided to the physician to assist the physician in evaluating the success or failure of the procedure. Preferably, after the ligament is reconstructed by being anchored within the two tunnels, a series of post-operative tests are conducted in order to test the patient's response to the surgery and to test the stability of the knee post surgery (post ligament reconstruction). In particular, the same laxity tests are conducted again in the same manner described earlier in reference to the pre-operative stage and the associated quantitative values for these laxity tests are displayed. Preferably, the screen is subdivided into regions that permit a graphic display and results for each laxity test to be shown, for example, simultaneously and thus, the physician can easily view the results of all the tests on a single screen. As with the pre-operative stage, the post-operative pivot shift test results are quantified in a number of different values, including the Delta Max value discussed earlier. An exit screen where the patient's report is provided and an option or command is provided to exit the application and burn the patient's report on a CD or the some other type of storage medium.

As previously mentioned, the present system 10 is also configured to assist the physician in deciding whether to perform an extra-articular ligament graft to improve exterior stabilization of the knee. For example, the physician will review all of the quantitative results obtained from the pre-operative laxity tests, as shown in the display screen of FIG. 13, and based upon the specific findings and values for this particular patient and based upon the physician's prior experience in interpreting such data, the physician is better guided in making a determination whether exterior stabilization is needed, thus requiring an extra-articular ligament graft. For example, now that the present invention permits a value to be calculated for the pivot shift test, the physician can evaluate this value and in his/her experience a pivot shift test value that is above a certain threshold may be an excellent indicator that the patient requires or would benefit from exterior stabilization of the knee.

If the physician decides to perform external stabilization of the knee, then the physician instructs or commands the system of such intent by pressing an icon or button on the user interface of the present system 10. For example, after the laxity test data is displayed as shown in FIG. 13, the physician can press a button or icon that is part of the display screen to command the system of such intent, thereby causing the system to display a new set of instructive screens to guide the physician through the process.

More specifically and according to one embodiment, FIGS. 19-21 are displays of screens that assist the physician in performing medial collateral ligament reconstruction, while FIGS. 22-26 are displays of screens that assist the physician in performing lateral collateral ligament reconstruction. Both medial and lateral reconstruction involves using the bone morphing features of the present invention to determine precise fixation locations that will yield the best results. FIG. 19 illustrates the first step of digitizing the femoral surface of insertion of the medial collateral ligament using the pointer 120 in the same manner described hereinbefore. Preferably, a number of acquired points (e.g., minimum 50 as shown in FIG. 19) are collected using the pointer 120 and the data processing system using the location data for the reference body 100 attached to the femur 2 and the pointer 120. Based on the collected data and bone morphing procedure, a realistic simulation of the whole digitized area and surrounding areas is created. The areas of higher accuracy can be, highlighted in the graphic representation since these areas represent the areas digitized using the pointer 120 (thus specific data has been acquired for each acquired point).

In medial collateral ligament reconstruction, the ligament is preferably attached to the tibial tunnel entrance (insertion point) which has been drilled in the tibia 4 and thus, this point is fixed, leaving it necessary only to locate the optimal point on the femur 2 to fix/anchor the MCL. FIG. 20 illustrates the digitization of the entrance or insertion point of the tibial tunnel using the pointer 120. The tibial tunnel in its entirety is shown in FIG. 20. Next and as shown in FIG. 21, a femoral point is selected using the pointer 120—in other words, the pointer 120 is used to digitize on the femur 2 the insertion point of the MCL. The selection of the femoral point with the pointer activates the anisometry map 300. Preferably, the bone morphing of the femur 2 provides the physician with a topographical view of the femur 2 as illustrated in FIG. 21 and this serves to guide the physician as to where the location may be to achieve optimal isometry.

FIG. 21 shows the checking of the anisometry of the MCL by evaluating the graph/plot 300 and the anisometry value (e.g., 5 mm in FIG. 21 example). The physician can redigitize the insertion point of the ligament on the femoral surface with the pointer 120 by simply running the pointer 120 along the bone surface and initiating the data collection process. FIG. 21 shows further checking and evaluation of the anisometry of the MCL and more particularly, simulated three-dimensional images of the femur 2 and the tibia 4 are shown with the tibial insertion point being indicated and the selected insertion point (where the pointer tip 124 is located) also being shown on the femoral surface. Graph 300 shows the anisometry characteristics of a ligament extending between these two highlighted points. As with the previously described ACL reconstruction, the physician, in real time, simply moves the pointer along the femoral surface and digitizes different points to evaluate the corresponding anisometry data for these points and a comparison of all these acquired points (prospective femoral insertion points) is conducted to determine which insertion point yields the best results in terms of anisometry values.

It will be appreciated that when the patient requires both MCL and ACL reconstruction, it is possible for a single ligament to be used by passing the ligament through the tibial tunnel and then looping it back exteriorly to the femoral insertion point to provide the desired exterior stabilization.

FIGS. 22-26 show how the present system can be used to perform lateral collateral ligament (LCL) reconstruction. FIG. 22 shows the use of the pointer 120 to widely digitize the femoral surface of insertion of the external lateral ligament and thus permit accurate bone morphing to be performed. FIG. 22 shows various acquired points on the femoral surface, with each acquired point being indicated by a dot or the like. Preferably, a minimum of 50 acquired points are collected, especially in the target area. The bone morphing results are displayed, with the more accurate areas of the femoral surface being differentiated from the surrounding areas, as by shadowing these areas or depicting these areas in a different color. Next and as shown in FIG. 23, the Gerdy's tubercle is digitized with the pointer 120. This point is used as the tibial insertion point for the lateral collateral ligament (LCL). FIG. 24 depicts the digitizing of the femur insertion point of the LCL with the pointer 120. Once again, the selection of the femoral point with the pointer 120 activates the anisometry map. The physician can select various femoral points until the optimal anisometry fit is achieved and as soon as this occurs, the physician is ready to drill the tunnel or hole to accommodate the LCL.

For both MCL and LCL reconstructions, the drill device 70 is preferably calibrated so that the tunnel or hole is formed with a high degree of precision.

In FIG. 25, the drill guide 78 of drill device 70 is navigated by aiming the planned points, which again are indicated and highlighted by bull's eyes. It is possible to re-plan these points with the pointer 120 or the guide. In FIG. 26, the anisometry of the LCL is checked and graph 300 provides the physician with the anisometry data and value, while the simulated bone morphs and locations of the respective tunnels and the LCL are shown.

As mentioned earlier, FIG. 27 is one of the final screens of the user interface that provide the physician with final comparison data to assess the success of the operation as well as various storage options for all of the collected data.

There are a number of advantages provided by the present system 10 and in particular, conventional systems required the laxity tests to be performed with mechanical devices and the physician would visually and temporally assess the knee condition, while the present system 10 permits the laxity tests to be performed visually and in a simulated manner and displayed on a screen easily viewed by the physician in real time. In addition, the present invention actually places and calculates a value for the pivot shift test which is of great assistance to the physician. To provide this type of simulated, visual results for the laxity tests using the system 10, the present inventors have discovered the importance of collecting and capturing lateral/medial glenoid data (while preserving the glenoid structures as opposed to shaving these structures as occurs in other procedures) which is used to formulate the laxity test results; and similarly, the present system acquires and collects data for the anterior inter-meniscal ligament, which is used to formulate the final value for the pivot shift test due to the anterior inter-meniscal ligament point being the preferred femoral reference point. More particularly, the present inventors have discovered that excellent results are yielded when the lateral and medial glenoid points are used as reference points on the tibial surfaces and are tracked as the laxity tests are performed and thus, the glenoid reference points are used in calculating one or more laxity values of the knee.

The following is one exemplary surgical protocol; however, it is not limiting of the present invention and it will be understood that other protocols are equally suitable.

1. Digitise Tibial malleoli
2. Record Leg in Extension position with neutral rotation
3. Flextion extension of leg with a "forced" posterior drawer to reduce laxity
4. Sagittal plane determined by fitting a plane to motion
5. Plane transformed to tibia from $1^{st}$ measurement
6. Digitize summit of external/internal spines of tibia
7. Digitize external/internal glenoid of tibia
8. Digitize middle of the anterior inter-meniscal ligament of tibia
9. Digitize middle of the arch of the femoral notch
10. Check of flexion angle
11. Morph tibial surface in the vicinity of the ACL attachment and check accuracy 12. Morph femoral notch surface in the vicinity of the ACL attachment and check accuracy
13. ANTERIOR DRAWER TEST—GUI displays relative position of tibia plus acquired tibial glenoid points with respect to femur in real time
14. MEDIAL LATERAL STABILITY TEST
15. LACHMAN TEST
16. PIVOT SHIFT TEST
17. Analyse kinematic data and display laxity results (max distances)
18. Navigation Thus, in one or more embodiments, the present invention can (1) provide an accurate system for positioning both intra-articular and extra-articular ligament grafts between at least two articulating bones of an joint; (2) can provide a method for realistic simulation of deformable ligament trajectories based on the three dimensional shape of the bones, the graft diameter, and the graft fixation points; (3) can provide a system for precisely measuring, analysing, and displaying knee joint laxities in translation and rotation for a set of prescribed knee motions; (4) can provide information on the shape of the bones intra-operatively without requiring expensive medical image data; (5) can provide isometric and impingement data for a ligament graft placement based on a realistic simulation of the trajectory of a deformable or bendable ligament graft; (6) can provide a system for passively guiding the drilling of bone tunnels to receive ligament grafts; (7) can provide data on the drill tunnel length for aiding implant screw sizing and selection; (8) can provide a system for comparing and storing preoperative and postoperative joint laxity data; and (9) optional the hip center can be acquired to determine global orientation of the femur.

For surgical procedures requiring restorative or reconstruction of ligaments in other locations of the body, bone morphology is preferably utilized to determine optimal parameters to minimize laxity in the resulting joint.

Thus, it will also be appreciated that while the present invention is discussed in terms of ligament reconstruction between the femur 2 and the tibia 4, it is not limited to such application but rather, it can be implemented in another application where two structures are movable relative to one another. Thus, one of these structures can be a hip bone and the other can be an adjacent bone.

While exemplary drawings and specific embodiments of the present invention have been described and illustrated, it is to be understood that the scope of the present invention is not to be limited to the particular embodiments discussed. Thus, the embodiments shall be regarded as illustrative rather than restrictive, and it should be understood that variations may be made in those embodiments by workers skilled in the art without departing from the scope of the present invention as set forth in the claims that follow, and equivalents thereof.

What is claimed is:

1. A computer assisted orthopedic surgery system for evaluating a ligament graft reconstruction procedure comprising:
   a position determining device configured to track the relative movements of a tibia bone and a femur bone of a knee using reference bodies that are attached to the tibia bone and the femur bone;
   a display; and
   a computer comprising:
      an initial generic model of a knee joint that is not specific to a patient, stored thereon, and
      software, stored thereon, when executed by the computer, performs the following steps to measure the laxity of the knee during a pivot shift test, the steps comprising:
         determining the three dimensional shape of the tibia bone and the femur bone in the vicinity of the articulating joint in response to a plurality of positions located using a tracking device and deforming the generic model of the knee joint based upon the determined three dimensional shape;
         tracking and recording a first motion path and a second motion path of the knee during a preoperative pivot shift motion test and a postoperative pivot shift motion test;
         determining a quantitative value associated with each of the preoperative and postoperative pivot shift motion tests by comparing the motion path of the respective pivot shift motion test to a motion path of a neutral flexion motion of the knee at any given degree of flexion;
         displaying on the display the first and second motion paths using the deformed generic model of the knee joint for evaluation by a user and the quantitative value; and
         generating preoperative and postoperative plots on the display that represent the knee laxity as a function of the degree of flexion of the knee during the preoperative and postoperative pivot shift motion tests, thereby allowing the user to compare the differences in the preoperative and postoperative pivot shift laxities.

2. The system of claim 1, wherein the quantitative value corresponds to a maximum translation value or a maximum rotation value that is calculated as the difference between the neutral motion path and the pivot shift motion path over a range of flexion, the difference being determined at the same degree of flexion for the neutral and the pivot shift motion paths.

3. The system of claim 2, wherein the tracking device is a tracked pointer that has a tip for digitizing reference points associated with the tibia and femur bones.

4. The system of claim 3, wherein at least one reference point on the tibia is used to plot the pivot shift test and/or to calculate the quantitative value, the at least one reference point being at least one point selected from the group consisting of a medial (internal) glenoid point, a lateral (external) glenoid point, and a middle of the anterior inter-meniscal ligament.

5. The system of claim 1, wherein the software is configured to provide instructions on the display and walk the user through the pivot shift test in real time as the user performs the respective pivot shift test.

6. The system of claim 1, wherein the position determining device is an emitter/detector tracking system, a reflector tracking system, an optical tracking system, an acoustic tracking system, a wave form tracking system, a shape based recognition tracking system, a video-based tracking system, a mechanical tracking system, a radio frequency tracking system, or combination thereof.

7. A computer assisted orthopedic surgery system for evaluating a ligament graft reconstruction procedure comprising:
   a position determining device configured to track the relative movements of a tibia bone and a femur bone of a knee using reference bodies that are attached to the tibia bone and the femur bone;

a display; and a computer comprising:

software, stored thereon, when executed by the computer, performs the following steps to measure the laxity of the knee during a pivot shift test, the steps comprising:

tracking and recording a first motion path and a second motion path of the knee during a preoperative pivot shift motion test and a postoperative pivot shift motion test;

determining a quantitative value associated with each of the preoperative and postoperative pivot shift motion tests by comparing the motion path of the respective pivot shift motion test to a motion path of a neutral flexion motion of the knee at any given degree of flexion;

displaying on the display the quantitative value; and generating preoperative and postoperative plots on the display that represent the knee laxity as a function of the degree of flexion of the knee during the preoperative and postoperative pivot shift motion tests, thereby allowing the user to compare the differences in the preoperative and postoperative pivot shift laxities.

8. The system of claim 7, wherein the quantitative value corresponds to a maximum translation value or a maximum rotation value that is calculated as the difference between the neutral motion path and the pivot shift motion path over a range of flexion, the difference being determined at the same degree of flexion for the neutral and the pivot shift motion paths.

9. The system of claim 8, wherein the system includes a tracked pointer that has a tip for digitizing reference points associated with the tibia and femur bones.

10. The system of claim 9, wherein at least one reference point on the tibia is used to plot the pivot shift test and/or to calculate the quantitative value, the at least one reference point being at least one point selected from the group consisting of a medial (internal) glenoid point, a lateral (external) glenoid point, and a middle of the anterior inter-meniscal ligament.

11. The system of claim 7, wherein the software is configured to provide instructions on the display and walk the user through the pivot shift test in real time as the user performs the respective pivot shift test.

12. The system of claim 7, wherein the position determining device is an emitter/detector tracking system, a reflector tracking system, an optical tracking system, an acoustic tracking system, a wave form tracking system, a shape based recognition tracking system, a video-based tracking system, a mechanical tracking system, a radio frequency tracking system, or combination thereof.

13. A computer assisted orthopedic surgery system for evaluating a ligament graft reconstruction procedure comprising:

a position determining device configured to track the relative movements of a tibia bone and a femur bone of a knee using reference bodies that are attached to the tibia bone and the femur bone;

a display; and a computer comprising:

software, stored thereon, when executed by the computer, is configured to:

track and record a first motion path and a second motion path of the knee during a preoperative pivot shift motion test and a postoperative pivot shift motion test, determine a quantitative value associated with each of the preoperative and postoperative pivot shift motion tests by comparing the motion path of the respective pivot shift motion test to a motion path of a neutral flexion motion of the, and displaying on the computer display the quantitative value and generate preoperative and postoperative plots on the computer display that represent the knee laxity of preoperative and postoperative pivot shift motion tests.

14. The system of claim 13, wherein the quantitative value corresponds to a maximum translation value or a maximum rotation value that is calculated as the difference between the neutral motion path and the pivot shift motion path over a range of flexion, the difference being determined at the same degree of flexion for the neutral and the pivot shift motion paths.

15. The system of claim 14, wherein the system includes a tracked pointer that has a tip for digitizing reference points associated with the tibia and femur bones.

16. The system of claim 15, wherein at least one reference point on the tibia is used to plot the pivot shift test and/or to calculate the quantitative value, the at least one reference point being at least one point selected from the group consisting of a medial (internal) glenoid point, a lateral (external) glenoid point, and a middle of the anterior inter-meniscal ligament.

17. The system of claim 13, wherein the software is configured to provide instructions on the display and walk the user through the pivot shift test in real time as the user performs the respective pivot shift test.

18. The system of claim 13, wherein the position determining device is an emitter/detector tracking system, a reflector tracking system, an optical tracking system, an acoustic tracking system, a wave form tracking system, a shape based recognition tracking system, a video-based tracking system, a mechanical tracking system, a radio frequency tracking system, or combination thereof.

* * * * *